(12) United States Patent
Glassman et al.

(10) Patent No.: US 8,058,509 B2
(45) Date of Patent: Nov. 15, 2011

(54) METHODS AND COMPOSITIONS FOR IN PLANTA PRODUCTION OF INVERTED REPEATS

(75) Inventors: Kimberly Glassman, Ankeny, IA (US); William J. Gordon-Kamm, Urbandale, IA (US); Rudolf Jung, Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 564 days.

(21) Appl. No.: 11/611,661

(22) Filed: Dec. 15, 2006

(65) Prior Publication Data

US 2007/0220628 A1 Sep. 20, 2007

Related U.S. Application Data

(60) Provisional application No. 60/752,352, filed on Dec. 21, 2005.

(51) Int. Cl.
*A01H 1/00* (2006.01)
*C12N 15/82* (2006.01)
*C12N 15/87* (2006.01)

(52) U.S. Cl. ........................................ 800/285; 800/278
(58) Field of Classification Search .................. None
See application file for complete search history.

(56) References Cited

U.S. PATENT DOCUMENTS

| 6,262,341 B1 | 7/2001 | Baszczynski |
| 6,331,661 B1 | 12/2001 | Baszczynski |
| 6,933,146 B2 | 8/2005 | Helliwell et al. |
| 7,102,055 B1 | 9/2006 | Baszczynski |
| 2004/0132042 A1* | 7/2004 | Frankard et al. .................. 435/6 |
| 2006/0143737 A1 | 6/2006 | Yadav |

FOREIGN PATENT DOCUMENTS

| EP | 1 080 208 | 3/2005 |
| WO | WO 2004/048581 | 6/2004 |
| WO | WO 2006/056617 | 6/2006 |

OTHER PUBLICATIONS

Marillonnet et al. 2004, PNAS 101:6852-6857.*

* cited by examiner

*Primary Examiner* — Li Zheng

(57) ABSTRACT

Methods and compositions are provided which allow for the production of an inverted repeat in a plant or plant part, which, when transcribed as an RNA can be used in some examples to decrease expression of a target polynucleotide of interest. The methods and composition provide precursor inverted repeat cassettes that are not capable of producing a hairpin RNA polynucleotide, and plants and plant parts comprising such precursor inverted repeat cassettes. The precursor inverted repeat cassettes are altered in planta by using a recombination system to produce a inverted repeat. Plants, plant parts, and seeds comprising the various components are also provided.

13 Claims, 5 Drawing Sheets

One transgenic line by simultaneous transformation of two T-DNA units (JT Super binary)
Cross to line w. active recombinase

METHODS AND COMPOSITIONS FOR IN PLANTA PRODUCTION OF INVERTED REPEATS

CROSS-REFERENCE TO RELATED APPLICATIONS

This application claims the benefit of U.S. Provisional Application No. 60/752,352, filed on Dec. 21, 2005 which is hereby incorporated by reference in its entirety.

FIELD OF THE INVENTION

The invention relates to site-specific recombination systems and the in planta production of inverted repeat polynucleotides.

BACKGROUND

RNA interference (RNAi) is a phenomenon in which small double-stranded RNA molecules induce sequence-specific degradation or inhibit the translation of homologous single-stranded RNA. In plants, RNAi can be induced through transfection or microinjection of long double-stranded RNA. The double-stranded RNA is cleaved into short RNA fragments of about 19 to 23 nucleotides (siRNAs). siRNAs are incorporated into a ribonuclease enzyme complex known as the RNA-induced silencing complex (RISC). The antisense strand of siRNA within the RISC pathway serves as a guide for sequence-specific degradation of homologous messenger RNAs.

The ability of transfected synthetic small interfering RNAs to suppress the expression of specific transcripts has proven to be a useful tool to study gene function. Recently short hairpin RNAs (shRNAs) have been shown to silence genes as effectively as short dsRNAs. Several DNA-based vectors have been developed that direct transcription of small hairpin RNAs (shRNAs). These RNAs are processed into functional siRNAs by cellular enzymes. RNAi vectors for the expression of shRNAs are available. These vectors typically use RNA polymerase III (Pol III) to express short hairpin RNAs. These transcripts adopt stem-loop structures that are processed into siRNAs by the RNAi machinery.

Other vectors have been developed that drive expression of both the sense and antisense strands of a DNA construct separately. The transcripts hybridize in vivo to make the siRNA. In efforts to induce long-term gene silencing, expression vectors that continually express siRNAs in stably transfected cells have been used.

One of the limitations in using hairpin technology for gene silencing is that silencing of many genes can be lethal or detrimental to recovering plants and/or progeny. In addition, another common problem is that assembly of hairpin DNA constructs in cloning vectors using routine molecular biology methods can often be difficult due to instability of such constructs in bacterial hosts used for cloning. Methods and compositions are needed in the art which improved the manner in which gene silencing is performed in plants.

SUMMARY

Methods and compositions are provided which allow for the production of an inverted repeat in a plant or plant part, which, when transcribed as an RNA can be used in some examples to decrease expression of a target polynucleotide of interest. The methods and composition provide precursor inverted repeat cassettes that are not capable of producing a hairpin RNA polynucleotides and plants and plant parts comprising such precursor inverted repeat cassettes. The precursor inverted repeat cassettes are altered in planta by using a recombination system to produce an inverted repeat. Plants, plant parts, and seeds comprising the various components are also provided.

DETAILED DESCRIPTION

Figure 1:
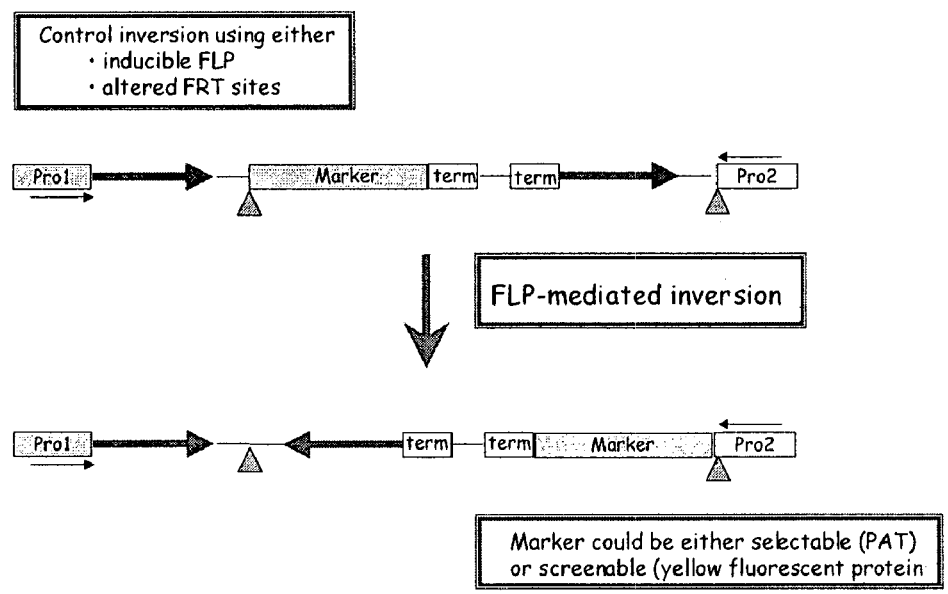
FIG. 1 provides a non-limiting schematic diagram of the use of an inverted repeat precursor cassette in combination with a recombination system to produce a inverted repeat. In this diagram, the arrow represents the target polynucleotide of interest to be silenced. Inversion of the transgenic fragment creates the inverted repeat and also turns on YFP marker expression, providing a visible marker for cells in which the inverted repeat has been formed.
Figure 2:
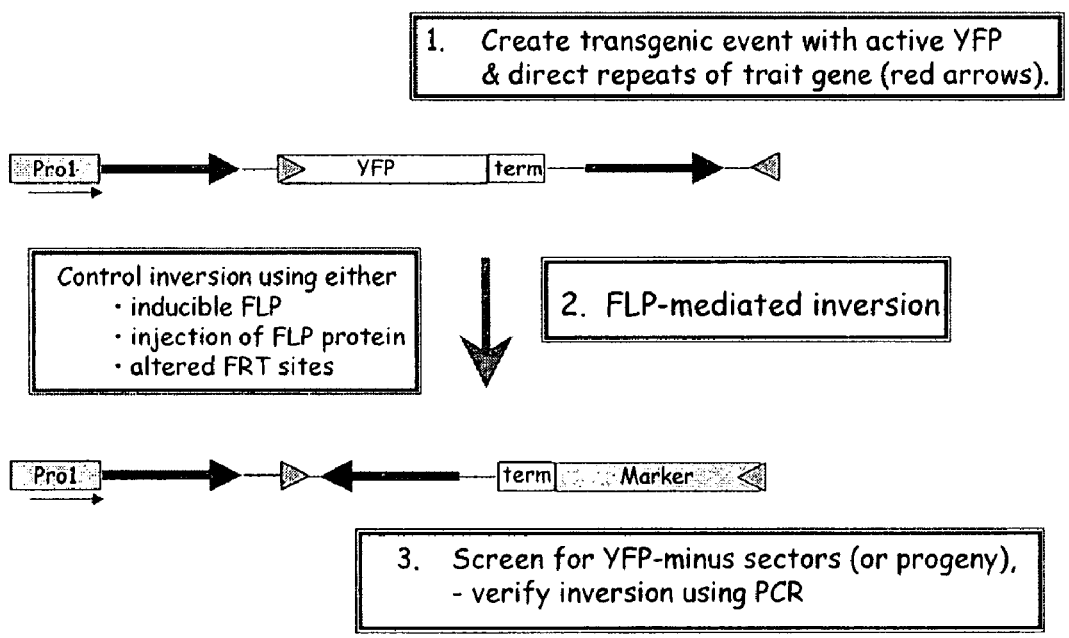
FIG. 2 provides a non-limiting schematic diagram of the use of an inverted repeat precursor cassette in combination with a recombination system to produce a inverted repeat. This scenario employs deletion of a blocking fragment to create the inverted repeat and loss of YFP expression.
Figure 3:
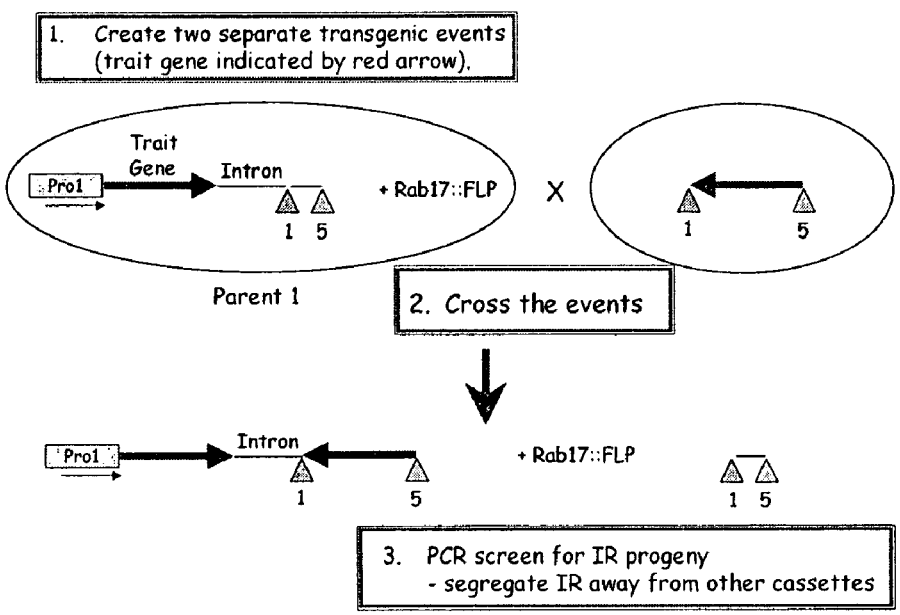
FIG. 3 provides a non-limiting schematic diagram of the use of an inverted repeat precursor cassette in combination with a recombination system to produce a inverted repeat. In this schematic, site-specific integration is used to insert a second polynucleotide comprising the inverted sequence at the recombination site to produce an inverted repeat.
Figure 4:
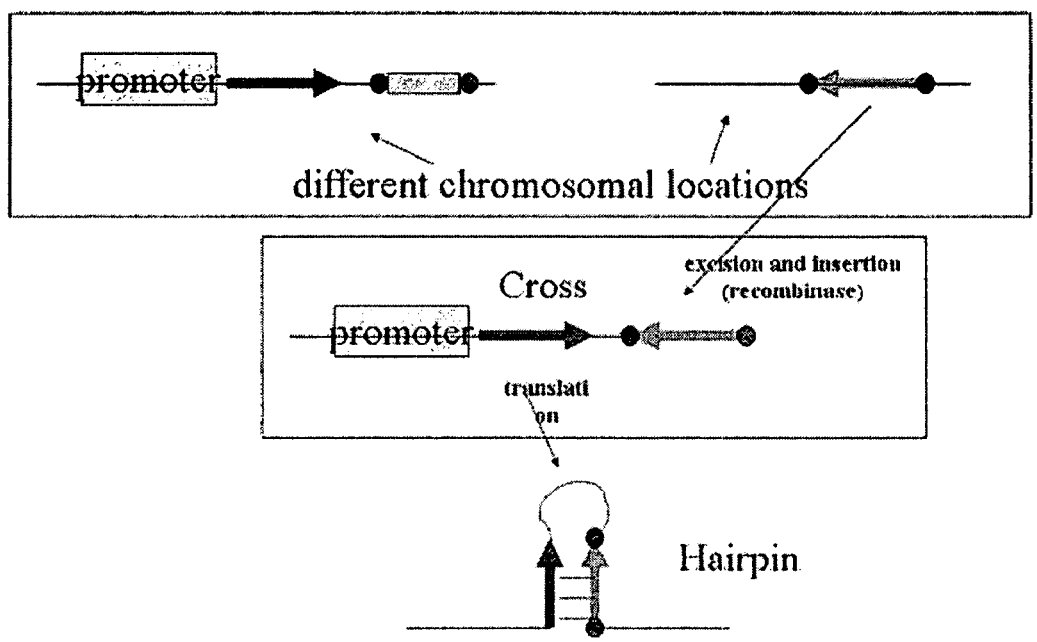
FIG. 4 provides a non-limiting schematic diagram of an inverted repeat precursor cassette. In this strategy, independent elements are introduced by simultaneous transformation with two T-DNA units during *Agrobacterium*-mediated transformation. The plant line comprising the inverted repeat precursor cassette and the second polynucleotide is crossed to a line expressing the appropriate recombinase.
Figure 5:
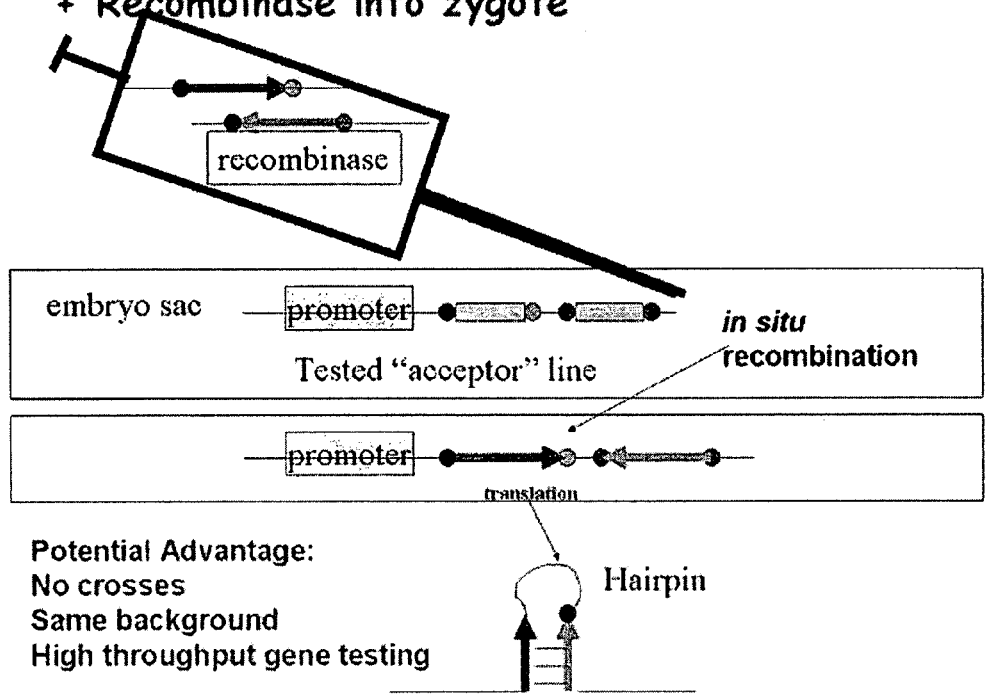
FIG. 5 provides a non-limiting schematic diagram of an inverted repeat precursor cassette. This strategy is based on a pre-selected tested acceptor line that comprises a promoter operably linked to four recombination sites. Complementary linear DNA fragments with matching recombination sites together with an active recombinase enzyme are injected into zygotic (or similar) tissues.

Many examples are provided herein which fully satisfy all applicable legal requirements, however the invention may be embodied in additional ways and is not limited to the examples presented herein, included within the scope of the appended claims. Although specific terms are employed herein, they are used in a generic and descriptive sense only and not for purposes of limitation. The article "a" and "an" are used herein to refer to one or more than one (i.e., to at least one) of the grammatical object of the article.

Methods and compositions related to hairpin formation and/or gene suppression are provided. Compositions include an inverted repeat precursor cassette and plants and plant parts having this inverted repeat precursor cassette. Using a recombinase system, the inverted repeat precursor cassette can be altered in planta to generate a inverted repeat. In some examples the inverted repeat RNA transcript forms a hairpin which can be designed to decrease expression of a target polynucleotide of interest. The methods and compositions provide various ways to both regulate the formation of the inverted repeat and to regulate the expression of the hairpin RNA. These various forms of regulation can be performed at different developmental stages of growth, in a manner that creates sectored plants if its desirable to compare silenced versus non-silenced tissues in the same plant, or in subsequent generations of plants.

Examples of the methods and compositions include the following:

1. A method for producing an inverted repeat in a plant or plant part comprising:
   a) introducing into the plant or the plant part a polynucleotide comprising an inverted repeat precursor cassette;
   b) introducing into said plant or the plant part a recombinase, said recombinase mediates a recombination event in said inverted repeat precursor cassette and thereby produces the inverted repeat.
2. The method of 1, further comprising expressing said inverted repeat in said plant or plant part, wherein said inverted repeat is transcribed to produce a hairpin RNA which decreases expression of a target polynucleotide of interest.
3. The method of 1 or 2, wherein said inverted repeat precursor cassette comprises an inversion inverted repeat precursor cassette.
4. The method of 3, wherein said inversion inverted repeat precursor cassette comprises a polynucleotide comprising in the 5' to 3' or the 3' to 5' orientation: a first DNA segment, a first recombination site, a second DNA segment, and a second recombination site; wherein,
   a) said first DNA segment comprises at least about 20 nucleotides having at least 90% sequence complementary to a target polynucleotide of interest; and,
   b) said second DNA segment comprises at least about 20 nucleotides having at least 85% sequence complementarity to the first DNA segment;
   c) said first and said second recombination sites are recombinogenic with respect to one another and are in inverted orientation with respect to one another; and,
   d) said first and said second DNA segment are in the same orientation with respect to one another.
5. The method of 4, wherein said inversion inverted repeat precursor cassette comprises the first DNA segment, the second DNA segment, and a third DNA segment, wherein said third DNA segment is of sufficient length to allow the functional inverted repeat expression unit to be transcribed as a hairpin RNA.
6. The method of 1 or 2, wherein said inverted repeat precursor cassette comprises an excision inverted repeat precursor cassette.
7. The method of 6, wherein said excision inverted repeat precursor cassette comprises the following in 5' to 3' or the 3' to 5' orientation: a first DNA segment, a first recombination site, a second recombination site, and a second DNA segment wherein
   a) said first DNA segment comprises at least about 20 nucleotides having at least 90% sequence complementary to a target polynucleotide of interest; and,
   b) said second DNA segment comprises at least about 20 nucleotides having at least 85% sequence complementarity to the first DNA segment;
   wherein said first and said second recombination sites are recombinogenic with respect to one another and are directly repeated with respect to one another; and, wherein and said first and said second DNA segments are in the opposite orientation with respect to another.
8. The method of 7, wherein said excision inverted repeat precursor cassette comprises the following in 5' to 3' or the 3' to 5' orientation: the first DNA segment, a third DNA segment, the first recombination site, the second recombination site, and the second DNA segment wherein said third DNA segment is of sufficient length to allow the functional inverted repeat expression unit to be transcribed as a hairpin RNA.
9. The method of 1 or 2, wherein said inverted repeat precursor cassette comprises a first DNA segment, and a first and a second functional recombination site, wherein said first and said second recombination sites are dissimilar and non-recombinogenic with respect to one another; and, said method further comprises introducing into the plant or plant part a second polynucleotide comprising a second DNA segment having sufficient sequence complementarity to the first DNA segment to form a hairpin RNA transcript and said second DNA segment is flanked by said first and said second recombination sites, such that the recombination inserts said second DNA segment into the precursor in the opposite orientation to said first DNA segment;
10. The method of 9, wherein the first DNA segment comprises at least about 20 nucleotides having at least 90% sequence complementary to a target polynucleotide of interest; and, the second DNA segment comprises at least about 20 nucleotides having at least 85% sequence complementarity to the first DNA segment.
11. The method of 9 or 10, wherein said inverted repeat precursor cassette comprises the following in 5' to 3' or the 3' to 5' orientation: the first DNA segment, a third DNA segment, and the first and the second recombination sites, wherein said third DNA segment is of sufficient length to allow the inverted repeat to be transcribed as a hairpin RNA.
12. The method of 9 or 10, wherein said second polynucleotide comprises the following in 5' to 3' or the 3' to 5' orientation: the first recombination site, a third DNA segment, the second DNA segment, and the second recombination site, wherein said third DNA segment is of sufficient length to allow the inverted repeat to be transcribed as a hairpin RNA.
13. The method of 1 or 2, wherein said inverted repeat precursor cassette comprises an insertion inverted repeat precursor cassette comprises a first recombination site, a second recombination site, a third recombination site, and a fourth recombination site, wherein said first, said second, said third and said fourth recombination sites are non-recombinogenic with respect to one another; and, said method further comprises introducing into the plant or the plant part a first polynucleotide comprising a first DNA segment flanked by said first and said second recombination sites; introducing into the plant or the plant part a second polynucleotide comprising a second DNA segment flanked by said third and said fourth recombination sites; wherein said first DNA segment comprises sufficient sequence complementarity to said second DNA segment to form a hairpin RNA transcript, wherein said recombinase recognizes and implements recombination at the first, the second, the third, and the fourth recombination sites such that upon integration of the first polynucleotide and the second polynucleotide at the appropriate recombination sites, the first and the second DNA segments are in the opposite orientation relative to one another.
14. The method of 13, wherein the first DNA segment comprises at least about 20 nucleotides having at least 90% sequence complementary to a target polynucleotide of interest; and, the second DNA segment comprises at least about 20 nucleotides having at least 85% sequence complementarity to the first DNA segment.
15. The method of 13 or 14, wherein said inverted repeat precursor cassette comprises in the following order the first recombination site, the second recombination site, a third DNA segment, the third recombination site, and the fourth recombination site, wherein said third DNA segment is of sufficient length to allow the inverted repeat to be transcribed as a hairpin RNA.

16. The method of 13 or 14, wherein said first or said second polynucleotide comprises a third DNA segment, wherein said third DNA segment is of sufficient length to allow the inverted repeat to be transcribed as a hairpin RNA.

17. The method of any one of 1-16, wherein said recombinase comprises a FLP recombinase, a Cre recombinase, a lambda integrase, a SSVI integrase, or a ϕ31C integrase.

18. The method of claim 9-16, wherein said recombinase comprises at least two different recombinases wherein at least one recombinase is a FLP recombinase, a Cre recombinase, a lambda integrase, a SSVI integrase, or an ϕ31C integrase.

19. The method of any one of 9-16, wherein said recombinase comprises a chimeric recombinase.

20. The method of 19, wherein said chimeric recombinase comprises a fusion protein comprising at least two different recombinases wherein at least one recombinase is a Cre recombinase, a FLP recombinase, a lambda integrase, a SSVI integrase, or a ϕ31C integrase.

21. The method of any one of 17, 18, or 20, wherein the FLP recombinase, the Cre recombinase, the lambda integrase, the SSVI integrase, or the +31C integrase is encoded by a polynucleotide having maize preferred codons.

22. The method of any one of 1-21, wherein introducing said inverted repeat precursor cassette comprises injection into an embryo sac, transformation, or sexual breeding.

23. The method of any one of 1-22, wherein introducing said recombinase comprises sexual breeding, transformation, or injection into an embryo sac.

24. The method of 9-12, wherein introducing said second polynucleotide comprises injection into an embryo sac, transformation, or sexual breeding.

25. The method of 13-16, wherein introducing at least one of said first polynucleotide or said second polynucleotide comprises injection into an embryo sac, transformation, or sexual breeding.

26. The method of 13-16, wherein said first polynucleotide, said second polynucleotide, and said recombinase are introduced by injection into the embryo sac.

27. The method of any one of 1-26, wherein a polynucleotide encoding said recombinase is stably integrated into a genome of said plant or said plant part.

28. The method of any one of 1-27, wherein said recombinase is encoded by a polynucleotide operably linked to a constitutive promoter active in the plant or the plant part.

29. The method of any one of 1-27, wherein said recombinase is encoded by a polynucleotide operably linked to an inducible promoter, a developmentally regulated promoter, or a tissue-preferred promoter, wherein the operably linked promoter is active in the plant or the plant part.

30. The method of any one of 1-26, 28, or 29, wherein said recombinase is transiently expressed in said plant or plant part.

31. The method of any one of 1-30, wherein said inverted repeat is operably linked to a constitutive promoter, an inducible promoter, a developmentally regulated promoter, or a tissue-preferred promoter, wherein the operably linked promoter is active in the plant or the plant part.

32. The method of any one of 1-31, wherein producing the inverted repeat activates a screenable marker.

33. The method of any one of 1-31, wherein producing the inverted repeat inactivates a screenable marker.

34. The method of claim 3-8, wherein said inversion inverted repeat precursor cassette or said excision inverted repeat precursor cassette comprises a set of corresponding, recombinogenic recombination sites.

35. The method of claim 3-8, wherein said inversion inverted repeat precursor cassette or said excision inverted repeat precursor cassette comprises a set of dissimilar, recombinogenic recombination sites.

36. The method of any one of 3-8, 34 or 35, wherein said inversion inverted repeat precursor cassette or said excision inverted repeat precursor cassette comprises a set of recombinogenic recombination sites selected from the group consisting of a FRT site, a LOX site or an att site.

37. The method of any one of 9-16, wherein said recombination sites are selected from the group consisting of a FRT site, a LOX site or an att site.

38. The method of any one of 1-37, wherein said plant or plant part is a monocot.

39. The method of 38, wherein said monocot is maize, barley, millet, wheat, sorghum, oat, or rice.

40. The method of any one of 1-37, wherein said plant or plant part is a dicot.

41. The method of claim 40, wherein said dicot is soybean, canola, alfalfa, sunflower, safflower, tobacco, *Arabidopsis*, or cotton.

42. The method of any one of 1-41, wherein said plant part comprises a plant cell.

43. A plant or plant part having stably integrated into its genome an excision inverted repeat precursor cassette or an inversion inverted repeat precursor cassette.

44. The plant or plant part of 43, wherein said inversion inverted repeat precursor cassette comprises a polynucleotide comprising the following in 5' to 3' or the 3' to 5' orientation: a first DNA segment, a first recombination site, a second DNA segment, and a second recombination site; wherein, a) said first DNA segment comprises at least about 20 nucleotides having at least 90% sequence complementary to a target polynucleotide of interest; and, b) said second DNA segment comprises at least about 20 nucleotides having at least 85% sequence complementarity to the first DNA segment;

c) said first and said second recombination sites are recombinogenic with respect to one another and are in inverted orientation with respect to one another; and, d) the first and the second DNA segments are in the opposite orientation with respect to one another.

45. The plant or plant part of claim 44, wherein said inversion inverted repeat precursor cassette comprises the first DNA segment, the second DNA segment, and a third DNA segment, wherein said second DNA segment comprises sufficient length to allow the inverted repeat to be transcribed as a hairpin RNA.

46. The plant or plant part of 43, wherein said excision inverted repeat precursor cassette comprises the following in 5' to 3' or the 3' to 5' orientation: a first DNA segment, a first recombination site, a second recombination site, and a second DNA segment wherein a) said first DNA segment comprises at least about 20 nucleotides having at least 90% sequence complementary to a target polynucleotide of interest; and, b) said second DNA segment comprises at least about 20 nucleotides having at least 85% sequence complementarity to the first DNA segment.

wherein said first and said second recombination sites of a) and b) are recombinogenic with respect to one another and are directly repeated with respect to one another; and, wherein said first and said second DNA segments of a) and b) are in the opposite orientation with respect to another.

47. The plant or plant part of claim 46, wherein said excision inverted repeat precursor cassette comprises the following in 5' to 3' or the 3' to 5' orientation: the first DNA segment, a third DNA segment, the first recombination site, the second recombination site, and the second DNA segment wherein said third DNA segment is of sufficient length to allow the functional inverted repeat expression unit to be transcribed as a hairpin RNA.

48. A plant or plant part comprising an insertion inverted repeat precursor cassette stably integrated into its genome, said insertion inverted repeat precursor cassette comprising a first DNA segment, and a first and a second recombination site, wherein said first and said second recombination sites are dissimilar and non-recombinogenic with respect to one another; and, a second polynucleotide comprising a second DNA segment having sufficient sequence complementarity to the first DNA segment to form a hairpin RNA transcript, said second polynucleotide is flanked by said first and said second recombination sites, and wherein the orientation of the second DNA segment is such that upon integration at the recombination sites said second DNA segment is inserted in the opposite orientation to said first DNA segment.

49. The plant or plant part of 48, wherein said second polynucleotide is stably integrated into a genome of the plant or plant part.

50. The plant or plant part of 48 or 49, wherein the first DNA segment comprises at least about 20 nucleotides having at least 90% sequence complementary to a target polynucleotide of interest; and, the second segment comprises at least about 20 nucleotides having at least 85% sequence complementarity to the first DNA segment.

51. The plant or plant part of 48-50, wherein said insertion inverted repeat precursor cassette comprises the following in 5' to 3' or the 3' to 5' orientation: the first DNA segment, a third DNA segment and the first and the second recombination sites, wherein said third DNA segment is of sufficient length to allow the inverted repeat to be transcribed as a hairpin RNA.

52. The plant or plant part of 48-50, wherein said second polynucleotide comprises the following in 5' to 3' or the 3' to 5' orientation: the first recombination site, a third DNA segment, the second DNA segment, and the second recombination site, wherein said third DNA segment is of sufficient length to allow the inverted repeat to be transcribed as a hairpin RNA.

53. A plant or plant part comprising an insertion inverted repeat precursor cassette stably integrated into its genome, said insertion inverted repeat comprising a first recombination site, and a second recombination site, a third recombination site, and a fourth recombination site, wherein said first, said second, said third and said fourth recombination sites are non-recombinogenic with respect to one another; and, said plant or plant part further comprises a first polynucleotide comprising a first DNA segment flanked by said first and said second recombination sites; and, a second polynucleotide comprising a second DNA segment flanked by said third and said fourth recombination site; wherein said first DNA segment comprises sufficient sequence complementarity to said second DNA segment to form a hairpin RNA transcript; and, the orientation of the first and the second DNA segments in the first and the second polynucleotides is such that upon recombination at the appropriate recombination sites, the first and the second DNA are inserted in the opposite orientation relative to one another.

54. The plant or plant part of 53, wherein the first DNA segment comprises at least about 20 nucleotides having at least 90% sequence complementary to a target polynucleotide of interest; and, the second DNA segment comprises at least about 20 nucleotides having at least 85% sequence complementarity to the first DNA segment.

55. The plant or plant part of 53 or 54, wherein said insertion inverted repeat precursor cassette comprises the following in 5' to 3' or the 3' to 5' orientation: the first target site, a third DNA segment and the second target site, wherein said third DNA segment is of sufficient length to allow the inverted repeat to be transcribed as a hairpin RNA.

56. The plant or plant part of 53 or 54, wherein said first or said second polynucleotide comprises a third DNA segment, wherein said third DNA segment is of sufficient length to allow the inverted repeat to be transcribed as a hairpin RNA.

57. The plant or plant part of any one of 43-56, wherein said plant or plant part further comprises a recombinase polypeptide.

58. The plant or plant part of 57, wherein said recombinase polypeptide is encoded by a polynucleotide stably integrated into a genome of the plant or plant part.

59. The plant or plant part of 57 or 58, wherein said recombinase comprises a FLP recombinase, a Cre recombinase, a lambda integrase, a SSVI integrase, or a φ31C integrase.

60. The plant or plant part of any one of 48-56, further comprising at least two different recombinases, wherein at least one recombinase is a FLP recombinase, a Cre recombinase, a lambda integrase, a SSVI integrase, or a φ31C integrase.

61. The plant or plant part of any one of 48-56, wherein said plant further comprises a chimeric recombinase.

62. The plant or plant part of 61, wherein said chimeric recombinase comprises a fusion protein comprising at least two different recombinases, wherein at least one recombinase is a Cre recombinase, a FLP recombinase, a lambda integrase, a SSVI integrase, or a φ31C integrase.

63. The plant or plant part of any one of 59-60, or 62, wherein the FLP recombinase, the Cre recombinase, the lambda integrase, the SSVI integrase, or the φ31C integrase is encoded by a polynucleotide having maize preferred codons.

64. The plant or plant part of any one of 57-63, wherein said recombinase is encoded by a polynucleotide operably linked to a constitutive promoter active in the plant or plant part.

65. The plant or plant part of any one of 57-63, wherein said recombinase is encoded by a polynucleotide operably linked to an inducible promoter, a developmentally regulated promoter, or a tissue-preferred promoter, wherein the operably linked promoter is active in the plant or plant part.

66. The plant or plant part of any one of 43-65, wherein upon forming a inverted repeat, said inverted repeat is operably linked to a constitutive promoter, an inducible promoter, a developmentally regulated promoter, or a tissue-preferred promoter, wherein the operably linked promoter is active in the plant or plant part.

67. The plant or plant part of 43-47, wherein said inversion inverted repeat precursor cassette or said excision inverted repeat cassette comprises a set of identical recombination sites.

68. The plant or plant part of 43-47, wherein said inversion inverted repeat precursor cassette or said excision inverted repeat cassette comprises a set of dissimilar recombination sites.

69. The plant or plant part of 43-47, wherein said inversion inverted repeat precursor cassette or said excision inverted repeat cassette comprises a set of recombinogenic recombination sites select from the group consisting of a FRT site, a LOX site, or an att site.
70. The plant or plant part of 48-56, wherein said recombination sites are selected from the group consisting of a FRT site, a Lox site or an att site.
71. The plant or plant part of any one of 43-70, wherein said plant or plant part is a monocot.
72. The plant or plant part of 71, wherein said monocot is from maize, barley, millet, wheat, sorghum, oat, or rice.
73. The plant or plant part of any one of 43-70, wherein said plant or plant part is a dicot.
74. The plant or plant part of 73, wherein said dicot is soybean, canola, alfalfa, sunflower, safflower, tobacco, *Arabidopsis*, or cotton.
75. The method of 1 or 2, wherein said inverted repeat precursor cassette comprises a first polynucleotide comprising a first DNA segment and a recombination site; and, said method further comprises introducing into the plant or plant part a second polynucleotide comprising a second DNA segment having sufficient sequence complementarity to the first DNA segment to form a hairpin RNA transcript, and said second polynucleotide is flanked by said first and said second recombination sites; and said recombinase recognizes and implements recombination at the first and the second recombination sites to insert the second DNA segment at the recombination site in the opposite orientation to said first DNA segment.

As used herein, an inverted repeat comprises an expression cassette with a promoter in functional proximity to a first DNA segment and a second DNA segment, wherein said first and said second DNA segments are in inverted orientation relative to each other, such that the first and second segments are transcribed as a single unit and the first and the second DNA segments have sufficient sequence complementarity to allow, upon transcription, the formation of a hairpin RNA transcript. In some examples the hairpin RNA transcript formed is designed to inhibit expression of a target polynucleotide of interest. The inverted repeat produced by the methods comprises a least one recombination site.

An inverted repeat precursor cassette comprises a construct having at least one recombination site, which upon a recombinase mediated modification to the cassette produces an inverted repeat capable of expressing a hairpin RNA transcript. Prior to a recombinase mediated modification in a plant, an inverted repeat precursor cassette is not able to express a hairpin RNA molecule. The inverted repeat precursor cassette can have a variety of structures including, but not limited to, an inversion inverted repeat precursor cassette, an excision inverted repeat precursor cassette, or an insertion inverted repeated cassette.

The methods and compositions employ various types and combinations of recombination sites. A recombination site is a polynucleotide sequence that is recognized by site-specific recombinase and that is recombinogenic with a second recombination site in the presence of the appropriate recombinase. Unless otherwise specifically stated, a recombination site is functional before and after the recombination reaction. Methods to determine if a recombination site is recombinogenic are known. The recombination sites employed in the methods and compositions can be corresponding sites or dissimilar sites. Corresponding recombination sites or a set of corresponding recombination are recombination sites having the same nucleotide sequence. Dissimilar recombination sites or a set of dissimilar recombination sites are recombination sites having distinct nucleotide sequences comprising at least one nucleotide difference. The recombination sites within a set of dissimilar recombination sites can be either recombinogenic or non-recombinogenic with respect to one another. Recombinogenic indicates that the set of recombination sites are capable of recombining with one another. Unless otherwise stated, recombinogenic recombination sites or a set of recombinogenic recombination sites include those sites where the relative excision efficiency of recombination between the sites is greater than 2%, 5%, 10%, 20%, 30%, 40%, 50%, 75%, 100%, or greater. The relative recombination excision efficiency is the excision efficiency in the presence of the native recombinase of a first recombination site with a second recombination site divided by the excision efficiency of a pair of the appropriate native recombination sites ×100%. For example, when working with dissimilar FRT sites, the relative recombination excision efficiency is defined as the excision efficiency in the presence of native FLP of a first dissimilar FRT site with a second dissimilar FRT site divided by the excision efficiency of a pair of native FRT sites (FRT1). Non-recombinogenic indicates that the set of recombination sites will not recombine with one another in the presence of the appropriate recombinase, or recombination between the sites is minimal. Unless otherwise stated, non-recombinogenic recombination sites or a set of recombinogenic recombination sites include those sites where the relative excision efficiency of recombination between the sites is lower than 2%, 1.5%, 1%, 0.75%, 0.5%, 0.25%, 0.1%, 0.075, 0.005%, 0.001%. Any suitable set of non-recombinogenic and/or recombinogenic recombination sites may be utilized, including a FRT site or functional variant or fragment thereof, a LOX site or functional variant or fragment thereof, a gix site or any functional variant or fragment thereof, a RS site or a functional variant or fragment thereof, or any combination thereof, an att site or any functional variant or functional fragment thereof, or any other combination of non-recombinogenic and/or recombination sites.

The orientation of the recombination sites can be manipulated in a variety of ways to construct a variety of inverted repeat precursor cassettes. Directly repeated indicates that the recombination sites in a set of recombinogenic recombination sites are arranged in the same orientation, such that recombination between these sites results in excision, of the intervening DNA sequence. Inverted recombination sites indicates that the recombination sites in a set of recombinogenic recombination sites are arranged in the opposite orientation, so that recombination between these sites results in inversion of the intervening DNA sequence.

In other examples, the inverted repeat precursor cassette and/or the transfer cassette can be composed of two or more modular segments. Modular segments of interest can include linkers, adapters, insulators, spacers, enhancers, restriction sites, recognition sites, binding sites, recombination sites, selectable markers, nucleotide sequences of interest, promoters, coding sequence, introns, 5' and 3' regulatory regions, entire expression cassettes, or combinations of the above. Each modular segment is delimited by flanking recombinase sites, and by using combinations of dissimilar recombinase sites, and/or distinct recombinases that recognize and recombine distinct recombinase target sites, or combinations of both, the individual modular segments can be modified independently.

In one example, the inverted repeat precursor cassette comprises an inversion repeat precursor cassette. An inversion inverted repeat precursor cassette comprises in the 5' to 3' or the 3' to 5' orientation: a first DNA segment, a first recombination site, a second DNA segment, and a second recombination site, wherein the first and the second DNA segments are in the same orientation with respect to one another. The first and the second DNA segments share sufficient sequence identity to form a hairpin RNA transcript. The first and the second recombination sites are recombinogenic with respect to one another and are in an inverted orientation with respect to one another. The inverted orientation of the recombination sites results in inversion of the DNA segment contained between them in the presence of an appropriate recombinase. The position of the recombination sites in the inversion inverted repeat expression cassette can vary so long as they allow for the formation of a inverted repeat upon the recombinase mediated event. Table 1 provides a variety of non-limiting examples of inverted repeat precursor cassettes and the resulting inverted repeat that result following the recombination event.

As exemplified in Table 1, marker sequences can be employed to monitor the recombination event and the formation of a inverted repeat. It is noted however, that marker sequences need not always be employed in an inversion inverted repeat precursor cassette. In addition, and as illustrated in Table 1, the inversion inverted repeat precursor cassette can be designed such that the marker sequence is either turned on or turned off following the formation of the inverted repeat.

The inversion inverted repeat precursor cassette can further include at least one intron. The intron can be positioned anywhere in the cassette. In one example, the position of the intron improves the transcription and/or stability of the transcript. In addition, the inversion inverted repeat precursor cassette can include a third DNA segment which is positioned in the precursor cassette, such that following the formation of the functional inverted repeat expression unit, the third DNA segment is positioned between the first and the second DNA segments of the inverted repeat and thereby allows a loop to form between the first and second elements in the hairpin RNA transcript. In some examples the third DNA segment can be intron.

In another example, the inverted repeat precursor cassette comprises an excision inverted repeat precursor cassette. An

TABLE 1

Non-limiting examples of inversion inverted repeat precursor cassettes

| Inversion Repeat Precursor Cassette | Inverted Repeat |
|---|---|
| pro(→)::R1::S1(←)::pro(←)::M(←)::R1::S2(←) | → pro(→)::R1::M(→)::pro(→)::S1(→)::R1::S2(←) |
| pro(→)::S1(→)::R1::pro(←)::S2(→)::R1::M(→) | → pro(→)::S1(→)::R1::S2(←)::pro(→)::R1::M(→) |
| pro(→)::S1(→)::atg(→)::R1::M(→)::S2(→)::R1::pro(←) | → pro(→)::S1(→)::atg(→)::R1::S2(←)::M(←)::R1::pro(←) |
| pro(→)::R1::L::S1(←)::pro(←)::M(←)::R1::S2(←) | → pro(→)::R1::M(→)::pro(→)::S1(→)::L::R1::S2(←) |
| pro(→)::S1(→)::L::R1::pro(←)::S2(→)::R1::M(→) | → pro(→)::S1(→)::L::R1::S2(←)::pro(→)::R1::M(→) |
| pro(→)::S1(→)::atg(→)::R1::M(→)::S2(→)::L::R1::pro(←) | → pro(→)::S1(→)::atg(→)::R1::L::S2(←)::M(←)::R1::pro(←) |
| pro(→)::S1(→)::R1::pro(←)::pro(→)::S2(→)::R1::M(→) | → pro(→)::S1(→)::R1::S2(←)::pro(←)::R1::M(→) | pro = promoter;
R1 = recombinogenic recombination site (either identical or dissimilar) in inverted orientation with respect to one another;
S1 = the first segment of the hairpin;
S2 = the second segment of the hairpin;
M = a screenable marker;
L = segment that allows a loop to form between S1 and S2;
(→) and (←) denotes the orientation of the elements. It is noted that inversion repeat precursor cassettes need not employ marker sequences.

The recombination sites employed in the inversion inverted repeat precursor cassette are in an inverted orientated with respect to one another and can be corresponding and recombinogenic with respect to one another, or alternatively, they can be dissimilar and recombinogneic with respect to one another. Such sets of recombinogenic and dissimilar recombination sites include combinations of lox sites such as lox43/lox44, lox66/lox71 and lox76/lox75 first reported by Albert et al. (1995) *The Plant Journal* 7:649-59. The use of such dissimilar, recombinogenic target sites flanking the inversion cassette are particularly useful, because the forward recombinase mediated reaction is favored over the reverse, which will increase the proportion of cells carrying the inverted sequence. Recombinases classified as integrases (for example, lambda, phiC31, SSV1 and TP901-1) also catalyze recombination between dissimilar, recombinogenic target sequences and can also be used, which will again favor a single, non-reversible inversion.

excision inverted repeat precursor cassette comprises in the 5' to 3' or the 3' to 5' orientation: a first DNA segment, a first recombination site, a second recombination site, and a second DNA segment. The first and the second DNA segments are in the same orientation with respect to one another, and the first and the second recombination sites are recombinogenic with respect to one another and are directly repeated with respect to one another. The first and the second DNA segments share sufficient sequence identity to form a hairpin RNA transcript. The directly repeated recombination sites result in excision of the sequence contained between them in the presence of an appropriate recombinase. Deletion of the insertion sequence allows the first and the second DNA segment to form a inverted repeat. Table 2 provides a variety of non-limiting examples of excision inverted repeat precursor cassettes and the inverted repeat produced following the recombination event.

TABLE 2

Non-limiting examples of excision inverted repeat precursor cassettes

| Excision Repeat Precursor Cassette | Inverted Repeat |
|---|---|
| pro(→)::S1(→)::R1::pro(→)::M(→)::R1::S2(←) | → pro(→)::S1(→)::R1::S2(←) |
| pro(→)::S1(→)::L::R1::pro(→)::M(→)::R1::S2(←) | → pro(→)::S1(→)::L::R1::S2(←) |
| pro(→)::S1(→)::R1::pro(→)::M(→)::R1::S2(←)::pro(←) | → pro(→)::S1(→)::R1::S2(←)::pro(←) | pro = promoter;
R1 = recombinogenic recombination site (either identical or dissimilar) in the same orientation with respect to one another;
S1 = the first segment of the hairpin;
S2 = the second segment of the hairpin;
M = a screenable marker;
L = segment that allows a loop to form between S1 and S2;

(→) and (←) denotes the orientation of the elements. It is noted that excision repeat precursor cassettes need not employ marker sequences.

The recombination sites employed in the excision inverted repeat precursor cassette can be corresponding and recombinogneic with respect to one another, or alternatively, they can be dissimilar and recombinogenic with respect to one another.

As exemplified in Table 2, marker sequences can be employed to monitor the recombination event and the formation of the inverted repeat. It is noted, however, that marker sequences need not always be employed in an excision inverted repeat precursor cassette. In addition, as illustrated in Table 2, the excision inverted repeat precursor cassette can be designed such that the marker sequence is either turned on or turned off following the formation of the inverted repeat.

The excision inverted repeat precursor cassette can further include at least one intron. The intron can be positioned any place in the cassette. In some examples, the position of the intron improves the transcription and/or RNA stability of the expression unit. In addition, the excision inverted repeat precursor cassette can include a third DNA sequence which is positioned in the precursor cassette, such that following the formation of the inverted repeat, the third DNA segment is located between the first and the second DNA segment and thereby allows upon transcription of the inverted repeat expression unit a loop to form between the first and the second segments.

In another example, the inverted repeat precursor cassette comprises an insertion inverted repeat precursor cassette. An insertion inverted repeat precursor cassette comprises a first DNA segment and a target site comprising at least a first recombination site. A transfer cassette is provided which comprises a second DNA segment and a recombination site that corresponds to the recombination site of the target site of the insertion inverted repeat precursor cassette. The orientation of the second DNA segment in the transfer cassette is such that upon integration of the transfer cassette at the target site, the second DNA segment is inserted in the opposite orientation to the first DNA segment. The second DNA segment is of sufficient sequence identity to the first DNA segment to allow for the formation of a hairpin RNA polynucleotide upon transcription from the inverted repeat.

In one example, the insertion inverted repeat precursor cassette comprises a first DNA segment and a target site comprising a first and a second recombination site, wherein the first and the second recombination sites are dissimilar and non-recombinogenic with respect to one another. A transfer cassette is provided which comprises a second DNA segment flanked by a first and a second recombination site that correspond to the sites that flank the target site of the insertion inverted repeat precursor cassette.

In other examples, the insertion inverted repeat precursor cassette comprises a polynucleotide comprising a first target site and a second target site, wherein the first target site comprises a first recombination site and a second recombination site, and the second target site comprises a third recombination site and a fourth recombination site. The first, second, third and fourth recombination sites are non-recombinogenic with respect to one another. In this example, the insertion inverted repeat precursor cassette is converted into a inverted repeat by introducing into the plant or plant part a first transfer cassette comprising a first DNA segment flanked by the first and the second recombination site and introducing into the plant or plant part a second transfer cassette comprising a second DNA segment flanked by the third and the fourth recombination site. The first DNA segment comprises sufficient sequence identity to the second DNA segment and the orientation of the first and the second DNA segments in the first and the second transfer cassette is such that upon the integration of the first transfer cassette at the first target site and upon the integration of the second transfer cassette at the second target site, the first and the second DNA are inserted in the opposite orientation relative to one another. For the formation of the inverted repeat a recombinase is introduced into the plant or plant part wherein the recombinase recognizes and implements recombination at the first, the second, the third, and the fourth recombination sites, thereby inserting the first transfer cassette at the first target site and inserting the second transfer cassette at the second target site.

As exemplified above, the insertion inverted repeat precursor cassettes employ target sites and transfer cassettes to allow for the formation of the inverted repeat in the plant or plant part. A target site comprises a polynucleotide that is immediately flanked by at least one recombination site. In some examples a target site comprises a polynucleotide flanked by two recombination sites that are dissimilar and non-recombinogenic with respect to one another. One or more intervening sequences may be present between the recombination sites of the target site. Intervening sequences of particular interest include linkers, adapters, screenable markers, insulators, enhancers, spacers, recognitions sites, binding sites, restriction sites, recombination sites, nucleotide sequences of interest, promoters, and/or other sites that aid in vector construction or analysis. A recombination site can be contained within introns, coding sequence, and/or 5' and 3' regulatory regions.

A transfer cassette comprises a polynucleotide flanked by a recombination site that is recombinogenic with a recombination site of the target site. In some examples the transfer cassette comprises a polynucleotide flanked by a first recombination site and a second recombination site, wherein the first and second recombination sites are dissimilar and non-recombinogenic with respect to one another and correspond to the recombination sites of the target site. The nucleotide sequence between the recombination sites of the target site will be exchanged with the nucleotide sequence between the recombination sites of the transfer cassette. Flanked by refers to a position immediately adjacent to the sequence intended to be exchanged, inverted, excised, or inserted.

The recombination sites of the transfer cassette or the target site may be directly contiguous with the intervening DNA segment or there may be one or more intervening sequences present between one or both ends of the DNA segment and the recombination sites. Intervening sequences of particular interest include linkers, adapters, screenable markers, regulatory regions, enhancers, insulators, spacers, recognition sites, binding sites, recombination sites, restriction sites, polynucleotides of interest, promoters and/or other sites that aid in vector construction or analysis. It is further recognized that the recombination sites can be contained within introns, coding sequence, or 5' and 3' untranslated regions.

Dissimilar and non-recombinogenic sites can be used in these examples including sites from multiple distinct recombination systems. For example, the first recombination site can be a lox site and the second recombination site can be a FRT site. In such examples, multiple recombinases can be provided or a single chimeric recombinase can be provided.

TABLE 3

Non-limiting examples of insertion inverted repeat precursor cassettes

| Insertion Inverted Repeat Precursor Cassette | Transfer cassette | Inverted Repeat |
|---|---|---|
| pro(→)::S1(→)::R1::R2 | + R1::S2(←)::R2 | → pro(→)::S1(→)::R1::S2(←)::R2 |
| pro(→)::S1(→)::intron::R1::R2 | + R1::S2(←)::R2 | → pro(→)::S1(→)::intron::R1:S2(←)::R2 |
| pro(→)::S1(→)::intron::R1::pro(→)::M(→)::R2 | + R1::S2(←)::R2 | → pro(→)::S1(→)::intron::R1:S2(←)::R2 |
| pro(→)::S1(→)::R1::R2 | + R1::intron::S2(←)::R2 | → pro(→)::S1(→)::R1::intron::S2(←)::R2 |
| R1::R2::S1(→) | + R1::pro(→)::S2(←)::R2 | → R1::pro(→)::S2(→)::R2::S1(→) |
| S1(→)::R1::R2 | + R1::S2(←)::pro(←)::R2 | → S1(→)::R1::S2(←)::pro(←)::R2 |
| pro(→)::S1(→)::L::R1::R2 | + R1::S2(←)::R2 | → pro(→)::S1(→)::L::R1:S2(←)::R2 |
| pro(→)::S1(→)::L::R1::pro(→)::M(→)::R2 | + R1::S2(←)::R2 | → pro(→)::S1(→)::L::R1:S2(←)::R2 |
| pro(→)::S1(→)::R1::R2 | + R1::L::S2(←)::R2 | → pro(→)::S1(→)::R1::L::S2(←)::R2 |
| pro(→)::R1::R2::R3::R4 | + R1::S1(→)::R2 and R3::S2(←)::R4 | → pro(→)::R1::S1(→)::R2::R3::S2(←)::R4 |
| R1::R2::R3::R4 | + R1::Pro(→)::S1(→)::R2 and R3::S2(←)::R4 | → R1::Pro(→)::S1(→)::R2::R3::S2(←)::R4 |
| R1::R2::L::R3::R4 | + R1::Pro(→)::S1(→)::R2 and R3::S2(←)::R4 | → R1::Pro(→)::S1(→)::R2::L::R3::S2(←)::R4 |
| pro(→)::R1::R2::R3::R4 | + R1::S1(→)::L::R2 and R3::S2(←)::R4 | → pro(→)::R1::S1(→)::L::R2::R3::S2(←)::R4 |
| pro(→)::S1(→)::R5 | + R5'::S2(←) | → pro(→)::S1(→)::R6::S2(←)::R6' |

Pro = promoter; R1, R2 = recombinogenic recombination site which are non-recombinogenic with respect to one another; S1 = the first segment of the hairpin; S2 = the second segment of the hairpin; M = a screenable marker; L = segment that allows a loop to form between S1 and S2; (→) and (←) denotes the orientation of the elements. R5 and R5' are dissimilar but recombinogenic recombination sites, for example such as aatB and attP. R6 and R6' are the products of recombination between R5 and R5', for example attL and attR. It is noted that insertion inverted repeat precursor cassettes need not employ marker sequences. The target sites of the inverted repeat precursor cassette are highlighted.

As demonstrated in Table 3, marker sequences can be employed to monitor the recombination event and the formation of the inverted repeat. It is noted that marker sequences need not always be employed in an insertion inverted repeat precursor cassette, in the transfer cassette or in the target site. In addition, as illustrated in Table 3, the insertion inverted repeat precursor cassette can be designed such that the marker sequence is either turned on or turned off following the formation of the inverted repeat.

The insertion inverted repeat precursor cassette or the transfer cassette can include at least one intron. In addition, the insertion inverted repeat precursor cassette or the transfer cassette can include a third DNA sequence which is positioned in the precursor cassette or the transfer cassette, such that following the formation of the inverted repeat, the third DNA segment is between the first and the second DNA segment and allows for the formation of a loop in a hairpin RNA transcript.

When the inverted repeat is transcribed, the resulting RNA transcript self-pairs and thereby comprises regions of double-stranded RNA. These transcripts are referred to herein interchangeably as hairpin RNA transcripts or hairpin RNA polynucleotides. In some examples these hairpin RNA transcripts can decrease the expression of one or more target polynucleotide of interest and/or polypeptide of interest.

An inhibitory hairpin RNA is capable of reducing or eliminating expression of a target polynucleotide or the polypeptide encoded thereby. The inhibitory hairpin RNA polynucleotide can reduce expression by influencing the level of the target RNA transcript or, alternatively, by influencing translation of the transcript. A single inverted repeat can be designed to decrease expression of a single polynucleotide, or of multiple target polynucleotides. Methods to assay for a inverted repeat that is capable of reducing or eliminating the level of a sequence of interest are known.

Methods for designing constructs that produce inhibitory RNA polynucleotides, along with their use in RNA interference to decrease or silence the expression of genes are described, for example, in Chuang and Meyerowitz (2000) *Proc. Natl. Acad. Sci. USA* 97:4985-90; Stoutjesdijk et al. (2002) *Plant Physiol* 129:1723-31; Waterhouse and Helliwell (2003) *Nat. Rev. Gen.* 4:29-38; Pandolfini et al. *BMC Biotechnology* 3:7, and U.S. Patent Application Publication No. 20030175965, each of which is herein incorporated by reference. For hairpin RNA (hpRNA) interference, typically the inverted repeat is designed to express an RNA transcript that pairs with itself to form a hairpin structure that comprises a single-stranded loop region and a base-paired stem. hpRNA molecules are highly efficient at inhibiting the expression of endogenous genes, and the RNA interference they induce is inherited by subsequent generations of plants. A transient assay for the efficiency of hpRNA constructs to silence gene expression in vivo has been described by Panstruga et al. (2003) *Mol. Biol. Rep.* 30:135-40, herein incorporated by reference.

In specific examples, the inverted repeat employed in the methods and compositions comprises a first segment, a third segment, and a second segment, where the first and the second segment share sufficient complementarity to allow the transcribed RNA to form a double-stranded stem-loop structure. Stem and loop structure and stem-loop structure are used synonymously herein and refer to mean a single RNA polynucleotide molecule wherein a region closer to the 5' end of the molecule pairs with a self-complementary region closer to the 3' end of the molecule to form a double-stranded RNA stem region while an intervening region between the 5' and 3' self-complementary regions remains as a unpaired loop. An RNA hairpin structure is an example of a stem-loop structure capable of causing RNA interference.

A loop or a loop region are used synonymously and indicate any nucleotide sequence that confers enough flexibility to allow self-pairing to occur between complementary regions of a polynucleotide. In some examples, the loop region may be substantially single stranded and act as a spacer between the self-complementary regions of the hairpin stem-loop. In some examples, the loop region can comprise a random or nonsense nucleotide sequence and thus not share sequence identity to a target polynucleotide. In other examples, the loop region comprises a sense or an antisense RNA sequence or fragment thereof that shares identity to a target polynucleotide. See, for example, International Patent Publication No. WO 02/00904, herein incorporated by reference.

In some examples, the loop region can comprise one or more spliceable introns. In intron-containing hairpin RNA (ihpRNA) constructs the inhibitory RNA transcripts have the same general structure as the hpRNA, but the RNA molecule additionally comprises an intron that is capable of being spliced in the cell. See, for example, Smith et al. (2000) *Nature* 407:319-320; Wesley et al. (2001) *The Plant Journal* 27:581-590; Wang and Waterhouse (2001) *Current Opinion in Plant Biology* 5:146-150; Waterhouse and Helliwell (2003) *Nat. Rev. Gen.* 4:29-38; Helliwell and Waterhouse (2003) *Methods* 30:289-95, and U.S. Patent Publication No. 20030180945, each of which is herein incorporated by reference. Any intron that is spliced may be used. Non-limiting examples of introns that may be used include the orthophosphate dikinase 2 intron 2 (pdk2 intron) described in U.S. Patent Application Publication No. 20030180945, the catalase intron from castor bean (GenBank Accession No. AF274974), the delta-12 desaturase (FAD2) intron from cotton (GenBank Accession No. AF331163), the delta-12 desaturase (FAD2) intron from *Arabidopsis* (GenBank Accession No. AC069473), the ubiquitin intron from maize (GenBank Accession No. S94464), an actin intron from rice, the maize ADHI intron1, the potato ST-LS1 intron2.

When the loop region does not contain an intron, it can be optimized to be as short as possible while still providing enough flexibility to allow the formation of the base-paired stem region. Accordingly, the loop sequence is generally less than 1000 nucleotides, less than 900 nucleotides, less than 800 nucleotides, less than 700 nucleotides, less than 600 nucleotides, less than 500 nucleotides, less than 400 nucleotides, less than 300 nucleotides, less than 200 nucleotides, less than 100 nucleotides, less than 50 nucleotides, less than 25 nucleotides, less than 20 nucleotides, less than 15 nucleotides or about 10 nucleotides or less.

The first and the second segment of the hairpin RNA molecule comprise the base-paired stem of the hairpin structure. In the inverted repeat, the first and the second segments are inverted repeats of one another and share sufficient complementarity to allow the formation of the base-paired stem region. In specific examples, the first and the second segments are fully complementary to the one another. Alternatively, the first and the second segment may be partially complementary to each other so long as they are capable of hybridizing to one another to form a base-paired stem region. The amount of complementarity between the first and the second segment can be calculated as a percentage of the entire segment. Thus, the first and the second segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the second segment are generally at least about 1000, 500, 400, 300, 200, 100, 50, 40, 30, 25, 20, 15 or 10 nucleotides in length. In specific examples, the length of the first and/or the second segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides. In other examples, the length of the first and/or the second segment comprises at least 10-20 nucleotides, 20-35 nucleotides, 30-45 nucleotides, 40-50 nucleotides, 50-100 nucleotides, or 100-300 nucleotides. See, for example, International Publication No. WO 0200904. In specific examples, the first and the second segment comprises at least 20 nucleotides having at least 85% complementary to the first segment. In other examples, the first and the second segments which form the stem-loop structure of the hairpin comprises 3' or 5' overhang regions having unpaired nucleotide residues.

In specific examples, the sequences used in the first, the second, and/or the third segments comprise domains that are designed to have sufficient sequence identity to a target polynucleotide of interest and thereby have the ability to decrease the level of expression of the target polynucleotide and/or any polypeptide encoded thereby. The specificity of the inhibitory RNA transcripts is generally conferred by these domains of the inverted repeat. In some examples, the first, second and/or third segment of the inverted repeat comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity or complementarity to the target polynucleotide to decrease expression of the target polynucleotide when the inverted repeat is expressed in an appropriate cell. In other examples, the domain is between about 15 to 50 nucleotides, about 20-35 nucleotides, about 25-50 nucleotides, about 20 to 75 nucleotides, about 40-90 nucleotides about 15-100 nucleotides. In specific examples, the domain of the first, the second, and/or the third segment has 100% sequence identity to the target polynucleotide. In other, the domain having homology to the target polynucleotide has at least 50%, 60%, 70%, 80%, 85%, 90%, 91%, 92%, 93%, 94%, 95%, 96%, 97%, 98%, 99%, or greater sequence identity to a region of the target polynucleotide, which is sufficient identity to decrease expression of the target polynucleotide and/or polypeptide of interest. In specific examples, a domain of the first, the second, and/or the third segment have 20, 15, 14, 13, 12, 11, 10, 9, 8, 7, 6, 5, 4, 3, 2, 1, or 0 differences as compared to a region of the target polynucleotide.

Any region of the target polynucleotide can be used to design the inverted repeat domain of the having sufficient sequence identity to allow the hairpin transcript to decrease the level of the target polynucleotide and/or polypeptide. The domain can be designed to share sequence identity to areas anywhere along the locus, to sequence within or between flanking regulatory sequences, to regulatory factors, to gene sequences, to coding sequences, and to sequences 150 kb in both either direction of a target polynucleotide. Also, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem.* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

In some examples, multiple members of a gene family can be targeted using the methods and compositions. For example, an inverted repeat can be designed based on sequence identity shared among various members of a gene family to target a common sequence domain, and thereby decrease the expression of multiple related polynucleotides. Alignment of the family members can be used to design such an inverted repeat.

In some examples, multiple unrelated target polynucleotides can also be targeted. For example, where the purpose is to decrease the level of expression of more than one target polynucleotide, regions of DNA whose sequence corresponds to at least one sequence in the different target polynucleotides can be combined into the first, second, and/or third segment of the inverted repeat. The inverted repeat is designed to express a single fusion RNA transcript having specificity for multiple target polynucleotides.

In some examples, the third segment may comprise all or part of a sequence corresponding to a target polynucleotide of interest. While the stem structure of the hairpin transcript will, in most instances, be designed to target a gene product, it is contemplated that the base-paired stem structure of the inhibitory RNA transcript may be formed by the hybridization of a first segment and a second segment, neither of which correspond to an endogenous sequence found in the organism of interest.

Expression of the inverted repeat can be controlled by convergent promoters. In this method, the inverted repeat is flanked by two convergent promoters that are oriented on either terminus of the inverted repeat. The same promoter or different promoters may be used. Each of the convergent promoters is operably linked to the inverted repeat. For example, a target site may be flanked by the convergent promoters and can comprise P1→::R1::S1(→)::S2(→)::R2::←P2, where P is apromoter, the shaded arrows indicate the direction of transcription for each promoter, R is a recombination site, S is the DNA segment, (→) (→) indicated the orientation of the DNA segments, and the :: indicates that the components are operably linked. See, for example, U.S. application Ser. No. 11/513,330 filed Aug. 26, 2006, herein incorporated by reference.

It is also recognized that a inverted repeat can be flanked by other elements that influence transcription. For example, insulator elements can flank the unit to minimize position effects. See, for example, U.S. Publication No. 2005/0144665, herein incorporated by reference. In other examples, the inverted repeat produced in the methods can comprise the first and the second DNA segments separated by the recombinase site, or the two inverted DNA segments can be separated by an intron in which the recombinase site is embedded.

Various assays can be employed to monitor the formation of a inverted repeat. In one example, the formation of a inverted repeat is assayed by monitoring the plant or plant part for the expected phenotype produced by suppression of the target polynucleotide by the inhibitory RNA polynucleotide.

In other examples, markers are employed in the inverted repeat precursor cassette and/or the transfer cassette and/or the target site and/or inverted repeat to monitor and/or select for formation of the inverted repeat. In one example, the marker employed to monitor the formation of the inverted repeat is a visual marker. In one example, the formation of the inverted repeat activates a visual marker, while in other examples, the formation of the inverted repeat deactivates the visual marker. A visual marker comprises a polynucleotide which encodes a product that can be readily visualized. Visual markers include, but are not limited to, various phenotypic markers such as galactosidase, GUS, CRC, anthocyanins, fluorescent proteins such as green fluorescent protein (GFP), cyan (CFP), yellow (YFP), red (RFP), and cell surface proteins. Visual markers also include the generation of new primer sites for PCR, such as those produced by the juxtaposition of two DNA sequence not previously juxtaposed, the inclusion of DNA sequences not acted upon or acted upon by a restriction endonuclease or other DNA modifying enzyme, chemical, etc.; and, the inclusion of a DNA sequences required for a specific modification such as methylation that allows its identification. In some examples, a screenable marker that provides a positive selection can be used, including markers that provide a growth advantage under certain conditions.

In other examples, the marker employed to monitor the formation of the inverted repeat is a selectable marker, such as a resistance marker including, but not limited to, an antibiotic resistance or an herbicide resistance gene. In one example, the formation of the inverted repeat activates a resistance marker, while in other examples, the formation of the inverted repeat deactivates the resistance marker. A resistance marker comprises a polynucleotide encoding a polypeptide that allows one to identify or select for or against a molecule or a cell that contains it under particular conditions that render the cells expressing the markers either resistant or sensitive to a particular set of conditions. These markers can encode an activity, such as, that encode products which provide resistance against otherwise toxic compounds such as antibiotics, including, spectinomycin, ampicillin, kanamycin, tetracycline, neomycin, kanamycin, G418 and hygromycin; polynucleotides that encode products which are otherwise lacking in the recipient cell such as tRNA genes, or auxotrophic markers. Additional selectable markers include genes that confer resistance to herbicidal compounds, such as glufosinate ammonium (BASTA™), bromoxynil, imidazolinones, cyanamide, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillen and Wissman (1989) *Topics Mol. Struc. Biol.* 10: 143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. Additional resistance markers of interest include anthocyanin genes such as C1 and R, bar, PAT, Hyg, GAT, CAH, ALS, and phosphomannose isomerase.

In some examples, a screenable marker that provides a positive selection can be used, including markers that provide a growth advantage under certain conditions. In other examples fusions between fluorescence markers and resistance markers, such as PAT~YFP are useful to follow formation of the inverted unit in both in culture and in the field.

The above list of markers is not meant to be limiting, any marker can be used. In some examples the polynucleotide encoding the marker can be modified to have a codon composition more similar to the codon usage typical for the host plant, plant cell, and/or organelle where the polynucleotide is expressed. The polynucleotide encoding the marker can further be modified to facilitate vector construction and/or analysis by the addition of diagnostic sequences such as restriction sites.

The methods and compositions employ at least one site-specific recombination system. Such systems are described, for example, in WO99/25821, WO99/25854, WO99/25840, WO99/25855, and WO99/25853, all of which are herein incorporated by reference. A recombinase is a polypeptide that catalyzes conservative site-specific recombination between its compatible recombination sites. The recombinase used can be a native recombinase or a biologically active fragment or variant of the recombinase. A native polypeptide or polynucleotide comprises a naturally occurring amino acid sequence or nucleotide sequence. For reviews of site-specific recombinases, see Sauer (1994) *Curr Op Biotechnol* 5:521-527; and Sadowski (1993) *FASEB* 7:760-767; the contents of which are incorporated herein by reference. Recombinases useful in the methods and compositions include recombinases from the Integrase and Resolvase families, biologically active variants and fragments thereof, and any other naturally occurring or recombinantly produced enzyme or variant thereof, that catalyzes conservative site-specific recombination between specified DNA recombination sites. Unless otherwise indicated, the recombinase is functional and maintains the ability to recombine appropriate recombinase sites.

The Integrase family of recombinases has over one hundred members and includes, for example, FLP, Cre, and lambda integrase (Enquiest et al. (1979) The role of lambda integrase in integration and excision. Cold Spring Harbor Symp. Quant. Biol. 43:1115-1120), phiC31, SSVI, TP901-1, Gin (Kahmann et al. (1985) *Cell* 25:729-736), HK022 (Kolot et al. (1999) *Mol. Biol. Rep.* 26:207-213), and R. For other members of the Integrase family, see for example, Esposito et al. (1997) *Nucleic Acids Res* 25:3605-3614 and Abremski et al. (1992) *Protein Eng* 5:87-91, both of which are herein incorporated by reference. Two common groups of integrases are the Tyrosine integrases and the Serine integrases. Examples of recombination systems include the streptomycete bacteriophage phi C31 (Kuhstoss et al. (1991) *J. Mol. Biol.* 20:897-908); the SSV1 site-specific recombination system from *Sulfolobus shibatae* (Muskhelishvili et al. (1993) *Mol. Gen. Genet.* 237:334-342); and a retroviral integrase-based integration system (Tanaka et al. (1998) *Gene* 17:67-76). In some examples, the recombinase does not require cofactors or a supercoiled substrate. Such recombinases include the native Cre, the native FLP, or active variants or fragments thereof, including FLPm (see, U.S. Pat. No. 5,929, 301) moCRE (see, U.S. Pat. No. 6,262,341), and FLP/Cre fusion recombinase (see, U.S. Pat. No. 6,262,341), all of which are herein incorporated by reference.

The FLP recombinase catalyzes a site-specific reaction that is involved in amplifying the copy number of the two-micron plasmid of *S. cerevisiae* during DNA replication. FLP recombinase refers to any recombinase that catalyzes site-specific recombination between two FRT sites. The FLP protein has been cloned and expressed. See, for example, Cox (1993) *Proc. Natl. Acad. Sci. USA* 80:4223-4227. The FLP recombinase may be derived from the genus *Saccharomyces*. One can also synthesize a polynucleotide comprising the recombinase using plant-preferred codons for enhanced expression in a plant of interest. A recombinant FLP enzyme encoded by a nucleotide sequence comprising maize preferred codons (FLPm) that catalyzes site-specific recombination events is known. See, for example, U.S. Pat. No. 5,929,301, herein incorporated by reference. Additional functional variants and fragments of FLP are known. See, for example, Buchholz et al. (1998) *Nat. Biotechnol.* 16:617-618, Hartung et al. (1998) *J. Biol. Chem.* 273:22884-22891, Saxena et al. (1997) *Biochim Biophys Acta* 1340(2):187-204, and Hartley et al. (1980) *Nature* 286:860-864, all of which are herein incorporated by reference.

The bacteriophage recombinase Cre catalyzes site-specific recombination between two lox sites. See, for example, Guo et al. (1997) *Nature* 389:40-46; Abremski et al. (1984) *J. Biol. Chem.* 259:1509-1514; Chen et al. (1996) *Somat. Cell Mol. Genet.* 22:477-488; Shaikh et al. (1977) *J. Biol. Chem.* 272: 5695-5702; and, Buchholz et al. (1998) *Nat. Biotechnol.* 16:617-618, all of which are herein incorporated by reference. The Cre polynucleotide sequences may be synthesized using plant-preferred codons. Such sequences (moCre) are described in WO 99/25840, herein incorporated by reference.

Recombinase polypeptides encoding the φC31 integrase, and nucleic acids that encode the recombinase polypeptides, are described in the art and can be obtained using routine methods. See, for example, Ow et al. (2002) *Plant Molecular Biology* 48:183-200, Thorpe et al. (1998) *Proc. Nat'l. Acad. Sci. USA* 95: 5505-5510; Kuhstoss et al. (1991) *J. Mol. Biol.* 222: 897-890; and U.S. Pat. No. 5,190,871 and U.S. Application Publication 2005/0054106. The φC31 integrase is also available from the Northern Regional Research Laboratories, Peoria, Ill. 61604) under the accession number B-18477.

When multiple recombination systems are employed, a chimeric recombinase can be used. A chimeric recombinase is a recombinant fusion protein which is capable of catalyzing site-specific recombination between recombination sites that originate from different recombination systems. For example, if a set of recombination sites, characterized as being dissimilar and non-recombinogenic with respect to one another, is utilized, and the set comprises a FRT site and a LoxP site, a chimeric FLP/Cre recombinase or active variant or fragment thereof can be provided, or both recombinases may be separately provided. Methods for the production and use of such chimeric recombinases or active variants or fragments thereof are described in WO 99/25840, herein incorporated by reference.

Fragments and variants of the polynucleotides encoding recombinases and fragments and variants of the recombinase proteins are also encompassed. A fragment is a portion of the polynucleotide and/or any polypeptide encoded thereby. Fragments of a polynucleotide may encode protein fragments, wherein the fragments retain the biological activity of the native protein and implement a recombination event. Thus, fragments of a polynucleotide may range from at least about 20 nucleotides, about 50 nucleotides, about 100 nucleotides, and up to the full-length polynucleotide encoding a recombinase.

A fragment of a polynucleotide that encodes a biologically active portion of a recombinase protein will encode at least 15, 25, 30, 50, 100, 150, 200, 250, 300, 320, 350, 375, 400, or 420 contiguous amino acids, or up to the total number of amino acids present in a full-length recombinase protein for example, 423 amino acids for the FLP recombinase and 338 amino acids for the Cre recombinase. A biologically active portion of a recombinase protein can be prepared by isolating a portion of a polynucleotide encoding a portion of the recombinase polypeptide, expressing the encoded portion of the recombinase protein, and assessing the activity of the portion of the recombinase. Polynucleotides that encode fragments of a recombinase polypeptide can comprise nucleotide sequence comprising at least 16, 20, 50, 75, 100, 150, 200, 250, 300, 350, 400, 450, 500, 550, 600, 650, 700, 800, 900, 1,000, 1,100, or 1,200 nucleotides, or up to the number of nucleotides present in a full-length recombinase nucleotide sequence, for example 1032 nucleotides for the FLP recombinase and 1260 nucleotides for the Cre recombinase.

Variant sequences have a high degree of sequence similarity. For polynucleotides, conservative variants include those sequences that, because of the degeneracy of the genetic code, encode the amino acid sequence of a native recombinase polypeptide. These variants can be identified with the use of well-known molecular biology techniques, as, for example, with polymerase chain reaction (PCR) and hybridization techniques. Variant polynucleotides also include synthetically derived nucleotide sequences, such as those generated, for example, by using site-directed mutagenesis but which still encode a recombinase protein. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by known sequence alignment programs and parameters.

Variants of a particular polynucleotide can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the recombinase are known. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A variant protein is a protein derived from the native protein by deletion addition, or substitution of one or more amino acids at any position(s) including the N-terminal and/or C-terminal end, or internal sites including conserved domains and/or motifs of the native protein. Variant proteins are biologically active, for example a variant recombinase can implement a recombination event between appropriate recombination sites. Such variants may result from, for example, genetic polymorphism or from human manipulation. Biologically active variants of a native recombinase protein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by known sequence alignment programs and parameters. A biologically active variant of a protein may differ from that protein by as few as 1-15 amino acid residues, as few as 1-10, such as 6-10, as few as 5, as few as 4, 3, 2, or even 1 amino acid residue.

Proteins may be altered in various ways including amino acid substitutions, deletions, truncations, and insertions. Methods for such manipulations are generally known. For example, amino acid sequence variants of the recombinase proteins can be prepared by mutations in the DNA. Methods for mutagenesis and nucleotide sequence alterations are well known. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the recombinase polynucleotides used includes both the naturally occurring sequences, as well as modified forms. Likewise, the proteins used encompass both naturally occurring proteins as well as variations and modified forms thereof. Such variants will continue to possess the ability to implement a recombination event. Generally, the mutations made in the polynucleotide encoding the variant polypeptide do not place the sequence out of reading frame or create complementary regions that could produce secondary mRNA structure. See, EP Patent Application Publication No. 75,444.

The deletions, insertions, and substitutions of the protein sequences are not expected to produce radical changes in the characteristics of the protein. The effect on activity of any substitution, deletion, insertion or combination thereof can be evaluated by routine screening assays. Assays for recombinase activity are known and generally measure the overall activity of the enzyme on DNA substrates containing recombination sites. For example, to assay for FLP activity, inversion of a DNA sequence in a circular plasmid containing two inverted FRT sites can be detected as a change in position of restriction enzyme sites. This assay is described in Vetter et al. (1983) *PNAS* 80:7284. Alternatively, excision of DNA from a molecule or intermolecular recombination frequency induced by the enzyme may be assayed, as described, for example, in Babineau et al. (1985) *J Biol Chem* 260:12313; Meyer-Leon et al. (1987) *Nucleic Acids Res* 15:6469; and Gronostajski et al. (1985) *J Biol Chem* 260:12328. Alternatively, recombinase activity may also be assayed by excision of a sequence flanked by recombinogenic FRT sites that upon removal will activate an assayable marker gene. Similar assay strategies may be used for Cre or other recombinase enzymes.

Variant polynucleotides and proteins also encompass sequences and proteins derived from a mutagenic and/or recombinogenic procedure such as DNA shuffling. With such a procedure, one or more different recombinase coding sequences can be manipulated to create a new recombinase protein possessing the desired properties. In this manner, libraries of recombinant polynucleotides are generated from a population of related polynucleotides comprising sequence regions that have substantial sequence identity and can be homologously recombined in vitro or in vivo. Strategies for such DNA shuffling are known. See, for example, Stemmer (1994) *Proc. Natl. Acad. Sci. USA* 91:10747-10751; Stemmer (1994) *Nature* 370:389-391; Crameri et al. (1997) *Nat. Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The methods and compositions employ recombination sites. A recombination site is a polynucleotide having a specific sequence that is recognized by the recombinase. Many recombination systems are known and one of skill will recognize the appropriate recombination site to be used with the recombination system of interest. Biologically active variants and fragments of recombination sites are also of use. Examples of recombination sites include FRT sites including, for example, the native FRT site (FRT1), and various functional variants of FRT, including but not limited to, FRT5, FRT6, FRT7, FRT87, and the variant FRT sites disclosed in U.S. application Ser. Nos. 11/487,273 and 11/487,300, filed Jul. 14, 2006. See, also, WO 03/054189, WO 02/00900, WO 01/23545, Senecoff et al. (1988) *J. Mol. Biol.* 201:406-421 and Voziyanov et al. (2002) *Nucleic Acids Res* 30:7, and, Schlake et al. (1994) *Biochemistry* 33:12745-12751, each of which is herein incorporated by reference.

Recombination sites from the Cre/Lox site-specific recombination system can also be used. Such recombination sites include, for example, native LOX sites and various functional variants of LOX. An analysis of the recombination activity of variant LOX sites is presented in Lee et al. (1998) *Gene* 216:55-65 and in U.S. Pat. No. 6,465,254, both of which are herein incorporated by reference. Also, see for example, Schlake and Bode (1994) *Biochemistry* 33:12746-12751; Huang et al. (1991) *Nucleic Acids Res* 19:443-448; Sadowski (1995) *In Progress in Nucleic Acid Research and Molecular Biology Vol.* 51, pp. 53-91; U.S. Pat. No. 6,465,254; Cox (1989) In *Mobile DNA,* Berg and Howe (eds) American Society of Microbiology, Washington D.C., pp. 116-670; Dixon et al. (1995) *Mol. Microbiol.* 18:449-458; Umlauf and Cox (1988) *EMBO* 7:1845-1852; Buchholz et al. (1996) *Nucleic Acids Res* 24:3118-3119; Kilby et al. (1993) *Trends Genet.* 9:413-421; Rossant and Geagy (1995) *Nat. Med.* 1: 592-594; Albert et al. (1995) *Plant J.* 7:649-659; Bayley et al. (1992) *Plant Mol. Biol.* 18:353-361; Odell et al. (1990) *Mol. Gen. Genet.* 223:369-378; Dale and Ow (1991) *Proc. Natl. Acad. Sci. USA* 88:10558-10562; Qui et al. (1994) *Proc. Natl. Acad. Sci. USA* 91:1706-1710; Stuurman et al. (1996) *Plant Mol. Biol.* 32:901-913; Dale et al. (1990) *Gene* 91:79-85; Albert et al. (1995) *Plant J.* 7:649-659; and WO 01/111058; all of which are herein incorporated by reference.

Recombination sites from the Int/att site-specific recombination systems can also be used. Such recombination sites include, for example, native att sites and various functional variants of att sites. See, for example, U.S. Application Publication No. 20040110293 and 20040253631, Groth et al. (2000) *Proc. Natl. Acad. Sci. USA,* 97: 5995, and Ow et al. (2002) *Plant Molecular Biology* 48:183-200.

A variant recombination site comprises a recombination site that is substantially similar to a native recombination site. Generally, modified recombination sites will have at least about 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the minimal native recombination site over its complete length or to any domain contained therein. The variant recombination site could therefore include 1, 2, 3, 4, 5, 8, 10, 12, 13, 14, 15, 16, 17, 18, 19, 20, 21, 22, 23, 24, 25, 28, 29 or greater nucleotide substitutions and/or deletions across the entire length of the minimal recombination site, or alternatively, in each of the various domains of the recombination site as outlined above.

The target sites and transfer cassettes can comprise sets of recombinogenic sites which are dissimilar and non-recombinogenic with respect to one another. Any suitable recombination site or set of recombination sites may be utilized, including a FRT site, a functional variant of a FRT site, a LOX site, and functional variant of a LOX site, a Gix site, a functional variant of a Gix site, a RS site or functional variant of a RS site, an att site, or a functional variant of an att site, or any combination thereof, or any other combination of recombination sites known. In one example, when recombinogenic and dissimilar recombination sites are employed in an inverted repeat precursor cassette, combinations of lox sites such as lox43/lox44, lox66/lox71 and lox76/lox75 first reported by Albert et al. (1995) *The Plant Journal* 7:649-59, are used. Additional dissimilar recombinogenic lox sites have been generated and can also be used. The use of such dissimilar, recombinogenic recombination sites flanking the inversion cassette are particularly useful, because the forward recombinase mediated reaction is favored over the reverse, which will increase the proportion of cells carrying the inverted sequence.

Methods of alignment of sequences for comparison are well known. The determination of percent sequence identity between any two sequences can be accomplished using a mathematical algorithm. Non-limiting examples of such mathematical algorithms are the algorithm of Myers and Miller (1988) *Comput. Appl. Biosci.* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci. USA* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix.

The various polynucleotides employed in the methods and compositions, including, but not limited to, the recombinase, the inverted repeat precursor cassette, or the transfer cassette can be provided in a DNA construct. The cassette can include 5' and 3' regulatory sequences operably linked to the appropriate DNA of interest. Alternatively, the DNA construct flanked by the appropriate recombination site can lack the 5' and/or 3' regulatory elements. In one instance, the DNA construct is designed such that in the presence of the appropriate recombinase a recombination event at the inverted repeat precursor cassette will result in the 5' and/or 3' regulatory regions being operably linked to the sequences of the DNA construct.

Generally, operably linked means that the nucleic acid sequences being linked are contiguous and, where necessary to join two protein coding regions, contiguous and in the same reading frame. However, it is recognized that intervening sequences can be present between operably linked elements and not disrupt the functional linkage. For example, an operable linkage between a promoter and a polynucleotide of interest comprises a linkage that allows for the promoter sequence to initiate and mediate transcription of the polynucleotide of interest. When used to refer to the linkage between a translational start and a recombination site, the term operably linked implies that the sequences are put together to generate an inframe fusion that results in a properly expressed and functional gene product. Similarly, when used to refer to the linkage between a promoter and a recombination site, the linkage will allow for the promoter to transcribe a downstream nucleotide sequence. The cassette may additionally contain at least one additional gene to be introduced into the organism. Alternatively, the additional gene(s) can be provided on multiple DNA constructs.

Such a DNA construct may be provided with a plurality of restriction sites or recombination sites for insertion of the sequence of interest to be under the transcriptional regulation of the regulatory regions. The expression cassette may additionally contain screenable marker genes.

In some examples, the DNA construct can include in the 5' to 3' direction of transcription, a transcriptional and translational initiation region, a polynucleotide of interest, and a transcriptional and translational termination region functional in the organism of interest. The transcriptional initiation region, the promoter, may be native, analogous, foreign, or heterologous to the host organism or to the DNA sequence to be expressed. Additionally, the promoter may be the natural sequence or alternatively a synthetic sequence. The termination region may be native or heterologous with the transcriptional initiation region, it may be native or heterologous with the operably linked polynucleotide of interest, or it may be native or heterologous with the host organism. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. The target polynucleotide to be suppressed can also be native or analogous or foreign or heterologous to the host organism.

Where appropriate, any sequence employed in the methods and compositions may be modified for expression in the transformed organism. For example, the genes can be synthesized using plant-preferred codons for improved expression. See, for example, Campbell and Gowri (1990) *Plant Physiol.* 92: 1-11 for a discussion of host-preferred codon usage. Methods are available for synthesizing plant-preferred genes. See, for example, U.S. Pat. Nos. 5,380,831, and 5,436,391, WO 99/25841, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell.

The DNA construct may additionally contain 5' leader sequences. Such leader sequences can act to enhance translation. Translation leaders are known and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods or sequences known to enhance translation can also be utilized, for example, introns, and the like.

In preparing the DNA construct, the various DNA fragments may be manipulated, to place the sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, transitions and transversions, may be involved. Generally, the DNA construct will comprise a marker gene for the selection of transformed cells.

Heterologous indicates that a polypeptide or a nucleotide sequence is a sequence that originates from a different species, or if from the same species, is substantially modified from its native form in composition and/or genomic locus.

Any promoter can be used to regulate expression of any component, or set of components of the system. A promoter is a region of DNA involved in recognition and binding of RNA polymerase and other proteins to initiate transcription. A plant promoter is a promoter capable of initiating transcription in a plant cell. Any promoter, or combination of promoters including by not limited to constitutive, inducible, developmentally/temporal, and/or spatially regulated promoter that is capable of regulating expression in the plant or plant part of interest may be used to express the appropriate component(s) of the system described herein.

The timing of the recombinase mediated event, along with the expression of the inverted repeat results in various outcomes. Accordingly, a variety of promoters can be employed to control either of these events. For, example, in specific examples, expression of at least one component of the system described herein, for example the inverted repeat or the recombinase is controlled by a constitutive promoter. Such promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142; and 6,177,611.

In other examples it may be beneficial to express at least one component of the system, for example the inverted repeat or the recombinase by an inducible promoter. Inducible promoters include pathogen-inducible promoters. Such as those from pathogenesis-related proteins (PR proteins), induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference. Promoters expressed locally at or near the site of pathogen infection include, for example, Marineau et al. (1987) *Plant Mol. Biol.* 9:335-342; Matton et al. (1989) *Mol Plant-Microbe Interact* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Additional promoters include the inducible promoter for the maize PRms gene, whose expression is induced by the pathogen *Fusarium moniliforme* (see, for example, Cordero et al. (1992) *Physiol. Mol. Plant. Path.* 41:189-200). Wound-inducible promoters include potato proteinase inhibitor (pin II) gene (Ryan (1990) *Ann. Rev. Phytopath.* 28:425-449; Duan et al. (1996) *Nat Biotechnol* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Lett* 323:73-76); MPI gene (Corderok et al. (1994) *Plant J.* 6(2): 141-150); and the like, herein incorporated by reference.

Chemical-regulated promoters can be used to express at least one component of the system, for example the inverted repeat or the recombinase. The promoter may be a chemical-inducible promoter, where application of the chemical induces gene expression, or a chemical-repressible promoter, where application of the chemical represses gene expression. Chemical-inducible promoters are known and include, but are not limited to, the maize In2-2 promoter, activated by benzenesulfonamide herbicide safeners (De Veylder et al. (1997) *Plant Cell Physiol.* 38:568-77), the maize GST promoter (GST-II-27, WO 93/01294), activated by hydrophobic electrophilic compounds used as pre-emergent herbicides, and the tobacco PR-1a promoter (Ono et al. (2004) *Biosci. Biotechnol. Biochem.* 68:803-7), activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to express at least one component of the system, for example the inverted repeat or the recombinase to target enhanced expression within a particular plant tissue. Tissue-preferred promoters include Kawamata et al. (1997) *Plant Cell Physiol.* 38(7): 792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2):525-535; Canevascini et al. (1996) *Plant Physiol.* 112(2):513-524; Lam (1994) *Results Probl. Cell Differ.* 20:181-196; and Guevara-Garcia et al. (1993) *Plant J.* 4(3):495-505.

Leaf-preferred promoters are known. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, promoter of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1): 1-22 (cytosolic glutamine synthase (GS), expressed in roots and root nodules of soybean). See also Bogusz et al. (1990) *Plant Cell* 2(7):633-641, where two root-specific hemoglobin gene promoters from *Parasponia andersonii* and *Trema tomentosa* are described. Leach and Aoyagi (1991) describe their analysis of the promoters of the highly expressed rolC and rolD root-inducing genes of *Agrobacterium rhizogenes* (see *Plant Sci* (Limerick) 79(1):69-76). They concluded that enhancer and tissue-preferred DNA determinants are dissociated in those promoters. Teeri et al. (1989) used reporter gene fusions to show that *Agrobacterium* T-DNA octopine synthase gene is especially active in the epidermis of the root tip and that TR1' and TR2' genes are root specific in intact plants and stimulated by wounding in leaf tissue (see *EMBO J.* 8(2):343-350). Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. Another root-preferred promoter includes the promoter of the phaseolin gene (Murai et al. (1983) *Science* 23:476-482 and Sengopta-Gopalen et al. (1988) *Proc. Natl. Acad. Sci. USA* 82:3320-3324.

Seed-preferred promoters include both those promoters active during seed development as well as promoters active during seed germination. See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase); (see WO 00/11177 and U.S. Pat. No. 6,225,529; herein incorporated by reference). For dicots, seed-preferred promoters include, but are not limited to, bean β-phaseolin, napin, β3-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, nuc1, etc. See also WO 00/12733, where seed-preferred promoters from end1 and end2 genes are disclosed; herein incorporated by reference.

In other examples expression of at least one component of the system, such as the functional inverted repeat expression unit or the recombinase, may be controlled by a developmentally regulated promoter. Such promoters are active in during specific developmental time periods.

In some examples—the nucleotide sequence encoding the recombinase is stably integrated into the genome of the plant or plant part. In other examples the recombinase is transiently present in the plant or plant part. Transient recombinase activity can be provided by transiently providing an expression cassette, providing the recombinase protein, or providing a recombinase mRNA. Controlling the delivery of the recombinase can be used to produce an inverted repeat within specific cells. These cells can then be selected to produce embryogenesic or organogenesic material capable of regenerating plants that are homogeneous for the inverted repeat. Alternatively, chimeric plants may be produced that may be useful to study gene function in the modified inverted-repeat sectors.

The developmentally regulated promoters or the inducible promoters employed can increase transcription of the recombinase or the inverted repeat during any stage of plant development including, but not limited to, the early stages of embryo development, the later stages of embryo development, during plant growth, during pollen shed, or during the development of reproductive structures such as, for example, the tassel or the ear.

The promoter(s) chosen to control expression of the inverted repeat will depend on the desired outcome. For example when expression of the inverted repeat is controlled by a constitutive promoter. a modified plant or plant part in which the inverted repeat is constitutively expressed in the plant or plant part is produced. Alternatively, the expression of the inverted repeat can also be controlled by an inducible promoter, a tissue-preferred promoter or a developmentally regulated promoter, or any combination thereof. Accordingly, modified plants or plant parts expressing an hairpin RNA polynucleotide in a specific set of tissues, at a specific developmental time period, or when the appropriate inducer is present at a sufficient level can be formed.

Polynucleotides include any nucleic acid polymer and can comprise deoxyribonucleotides, ribonucleotides and combinations of ribonucleotides and deoxyribonucleotides. Such deoxyribonucleotides and ribonucleotides include both naturally occurring molecules and synthetic analogues. The polynucleotides also encompass all forms of sequences including, but not limited to, single-stranded forms, double-stranded forms, hairpins, stem-and-loop structures, and the like.

Various plant species can be used in the methods and compositions including, but not limited to, monocots and dicots. Examples of plant genuses and species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (Glycine max), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena*), barley (*Hordeum*), *Arabidopsis*, vegetables, ornamentals, grasses, and conifers. Additional plants of interest include crop and grain plants that provide seeds of interest, oil-seed plants, and leguminous plants. Leguminous plants include beans and peas. Beans, besides those noted above include guar, locust bean, fenugreek, garden beans, cowpea, mungbean, lima bean, fava bean, lentils, chickpea, and castor, etc. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The term plant includes plant cells, plant protoplasts, plant cell tissue cultures from which plants can be regenerated, plant calli, plant clumps, and plant cells that are intact in plants or parts of plants such as embryos, pollen, ovules, seeds, flowers, kernels, ears, cobs, husks, stalks, roots, root tips, anthers, and the like. Plants, plant parts, and seed are provided having stably incorporated into their genome an inverted repeat precursor cassette. Such inverted repeat precursor cassettes include excision, insertion and inversion precursor cassettes.

In one example, plants, plant parts, and seeds are provided which comprise an insertion inverted repeat precursor cassette stably integrated into the genome. The insertion inverted repeat precursor cassette can comprise a first DNA segment and a target site comprising a first and a second recombination site, wherein the first and the second recombination sites are dissimilar and non-recombinogenic with respect to one another. The plant, plant part or seed further comprises a transfer cassette comprising a second DNA segment having sufficient sequence complementarity to the first DNA segment to produce a hairpin RNA transcript. The transfer cassette is flanked by the first and the second recombination sites, such that upon integration of the transfer cassette at the target site, the second DNA segment is inserted in the opposite orientation to the first DNA segment. In some examples, the transfer cassette, prior to insertion into the target site, is stably incorporated into the genome of the plant, plant part or seed.

In other examples, the insertion inversion repeat precursor cassette comprises a first DNA segment and a target site comprising a first recombination site. The plant, plant part or seed further comprises a transfer cassette comprising a second DNA segment and a the first recombination site, such that upon integration of the transfer cassette at the target site, the second DNA segment is inserted in the opposite orientation to the first DNA segment. In some examples the transfer cassette comprise the second DNA segment and a second recombination site, wherein the second recombination site is dissimilar and recombinogenic with the first recombination site of the precursor cassette.

In other examples, plants, plant parts and seeds having an insertion inverted repeat precursor cassette stably integrated into the genome of the plant, plant part, or seed, wherein the insertion inverted repeat comprises a first target site and a second target site are provided. The first target site comprises a first recombination site and a second recombination site, and the second target site comprises a third recombination site and a fourth recombination site, wherein the first, the second, the third and the fourth recombination sites are non-recombinogenic with respect to one another. The plant, plant part, or seed further comprises a first transfer cassette comprising a first DNA segment flanked by the first and the second recombination sites; and, a second transfer cassette comprising a second DNA segment flanked by the third and the fourth recombination sites. Neither, one or both of these transfer cassettes can be stably integrated into the genome of the plant, plant part or seed. The first DNA segment comprises sufficient sequence to the second DNA segment to form a hairpin RNA. The orientation of the first and the second DNA segments in the first and the second transfer cassette is such that upon integration of the first transfer cassette at the first target site and upon the integration of the second transfer cassette at the second target site, the first and the second DNA are inserted in the opposite orientation relative to one another.

Any of the plants, plant parts and seeds can further comprise a recombinase polypeptide, or a polynucleotide encoding the recombinase polypeptide which is either transiently expressed or stably incorporated into the genome of the plant or plant part or seed.

The methods and compositions allow various ways to regulate the formation of the inverted repeat and expression of the hairpin RNA. The regulation can be performed at different developmental stages of growth, in a manner that creates sectored plants, for example (if its desirable to compare silenced versus non-silenced tissues in the same plant), or in subsequent generations of plants. Accordingly, the plants can be sectored wherein they express the hairpin RNA polynucleotide in a subset of tissues or cell type. In other examples, cells having the inverted repeat can be selected, embryogenic and/or organogenic material produced, which can optionally be regenerated into a plant that is homozygous for the inverted repeat.

Any means can be used to bring together the various components of the system. A variety of methods are known for the introduction of nucleotide sequences and polypeptides into an organism, including, for example, transformation, sexual crossing, injection of polynucleotides or polypeptides into the embryo sac of a plant, and the introduction of the polypeptide, DNA, or mRNA into the cell. See, also, WO99/25884 herein incorporated by reference. Introducing indicates that a composition comprising at least one molecule, polynucleotide, and/or polypeptide is presented to the plant, plant part, or plant cell at least one molecule, in such a manner that the composition gains access to the interior of a cell. The methods do not depend on a particular method for introducing a composition to a plant, only that the composition gains access to the interior of at least one cell of the plant.

Providing refers to any method that allows for a composition, polypeptide and/or a polynucleotide to be brought together with the recited components. For instance, a cell can be provided with various components via a variety of methods including but not limited to transient and stable transformation methods; co-introducing a recombinase DNA, mRNA or protein directly into the cell; injecting the DNA, mRNA, or protein into the embryo sac; injecting an *Agrobacterium* comprising the DNA into an embryo sac, employing a plant or cell strain or line that express the recombinase for the initial transformation; or growing/culturing the plant or plant part carrying the inverted repeat precursor cassette and crossing it to an plant that expresses an active recombinase protein and selecting events in the progeny.

Methods for providing or introducing a composition into various plants are known including, but not limited to, stable transformation methods, transient transformation methods, virus-mediated methods, injection into the embryo sac, and sexual breeding. Stable transformation indicates that the introduced polynucleotide integrates into a genome of the plant, plant part, or plant cell and is capable of being inherited by progeny thereof. Transient transformation indicates that the introduced composition is only temporarily expressed or present in the plant, plant part, or plant cell.

Protocols for introducing polynucleotides and polypeptides into plants may vary depending on the type of plant or plant cell, for example monocot or dicot, targeted for transformation. Suitable methods of introducing polynucleotides and polypeptides into plant cells and subsequent insertion into the plant genome include microinjection (Crossway et al. (1986) *Biotechniques* 4:320-334; and U.S. Pat. No. 6,300,543), meristem transformation (U.S. Pat. No. 5,736,369), electroporation (Riggs et al. (1986) *Proc. Natl. Acad. Sci. USA* 83:5602-5606, liposomes, *Agrobacterium*-mediated transformation (U.S. Pat. No. 5,563,055; and U.S. Pat. No. 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and, McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783, and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Rep* 12:250-255; Christou and Ford (1995) *Annals of Botany* 75:407-413 (rice); and, Osjoda et al. (1996) *Nature Biotechnol* 14:745-750 (maize via *Agrobacterium tumefaciens*); all of which are herein incorporated by reference.

Alternatively, the various polynucleotides employed in the methods and compositions may be introduced into plants by contacting plants with a virus or viral nucleic acids. Generally, such methods involve incorporating a polynucleotide within a viral DNA or RNA molecule. A polypeptide of interest may be initially synthesized as part of a viral polyprotein, which later may be processed by proteolysis in vivo or in vitro to produce the desired recombinant protein. Further, it is recognized that promoters also encompass promoters utilized for transcription by viral RNA polymerases. Methods for introducing polynucleotides into plants and expressing a protein encoded therein, involving viral DNA or RNA molecules, are known. See, for example, U.S. Pat. Nos. 5,889,191, 5,889,190, 5,866,785, 5,589,367 and 5,316,931; herein incorporated by reference.

Transient transformation methods include, but are not limited to, the introduction of polypeptides directly into the plant, the introduction of polynucleotides such as DNA and/or RNA polynucleotides, and the introduction of the RNA transcripts into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci. USA* 91: 2176-2180; and, Hush et al. (1994) *J Cell Sci* 107:775-784, all of which are herein incorporated by reference.

In one example, one or more of the components is stably incorporated into the genome of a plant which is then sexually crossed to a plant having one or more other components to produce a inverted repeat. For example, an "-acceptor plant-" having stably incorporated into its genome an inverted repeat precursor cassette can be crossed to a plant having stably incorporated an expression cassette encoding a recombinase polypeptide. Upon crossing these lines together, progeny carrying both the recombinase polynucleotide and the inverted repeat precursor cassette are generated. A plant carrying a inverted repeat can then be formed.

In other examples, the acceptor plant has stably incorporated into its genome an insertion inverted repeat precursor cassette. The acceptor is crossed to a plant having stably incorporated into its genome at least one of the first transfer cassette, a second transfer cassette and/or the polynucleotide encoding the recombinase. Multiple crosses and progeny selection steps can be performed to cross each necessary component into the acceptor line in order to generate a plant having a inverted repeat.

In another example, at least one composition such as a polynucleotide and/or polypeptide is injected into an unfertilized or a fertilized embryo sac. In one example, the injected polynucleotides are contained in *Agrobacterium* which is microinjected directly to the embryo sac of the plant. Such an injection method allows for various components to be introduced into the cellular environment of the embryo sac, which represents a cellular environment close to that in which recombination is known to occur naturally. In one such method, an effective concentration of an *Agrobacterium* comprising a T-DNA comprising at least one component such as, the inverted repeat precursor cassette, a transfer cassette, the recombinase polypeptide, and/or a polynucleotide encoding the recombinase is injected into an embryo sac. In specific examples, the polynucleotide(s) and/or polypeptide(s) introduced in this matter is stably integrated into the genome of the egg cell, zygote, embryo, or endosperm. Such methods are disclosed in more detail in U.S. application Ser. Nos. 11/427,371, filed Jun. 29, 2006, published as US 2007-0143880, and 11/427,947, filed Jun. 30, 2006, published as US 2007-0143881, the contents of both of these applications are herein incorporated by reference in their entirety.

Transfer DNA or T-DNA comprises a genetic element that is capable of integrating a polynucleotide contained within its borders into another polynucleotide. The T-DNA can comprise the entire T-DNA, but need only comprise the minimal sequence necessary for cis transfer, for example the right or left border. The T-DNA can be synthetically derived or can be from an *Agrobacterium rhizogene* Ri plasmid or from an *Agrobacterium tumefaciens* Ti plasmid, or functional derivatives thereof. Any desired polynucleotide, for example, a recombinase, a polynucleotide of interest, a target site, a transfer cassette, and/or a marker sequence may be positioned between the left border sequence and the right border sequence of the T-DNA. The sequences of the left and right border sequences may or may not be identical and may or may not be inverted repeats of one another. It is also possible to use only one border, or more than two borders, to accomplish the introduction of a desired polynucleotide.

The cells that have had the sequence introduced may be grown into plants in accordance with conventional ways. See, for example, McCormick et al. (1986) *Plant Cell Rep* 5:81-84. These plants may then be grown, and self-pollinated, backcrossed, or outcrossed the resulting progeny expressing the desired phenotypic characteristic and/or comprising the introduced polynucleotide or polypeptide identified. Two or more generations may be grown to ensure that expression is stably maintained and inherited and the seeds harvested. In this manner, transformed seed are generated.

A decreased level or decreasing the level or decreased expression of a polynucleotide or a polypeptide refers to any decrease in the expression, concentration, and/or activity of a polynucleotide and/or polypeptide gene product including any relative increment in expression, concentration and/or activity. Expression refers to the biosynthesis of that product including the transcription or translation of the gene product. In general, the level of the polypeptide or the polynucleotide is decreased by at least 1%, 5%, 10%, 20%, 30%, 40%, 50%, 60%, 70%, 80%, 90%, 95%, or greater relative to a native control plant, plant part, or cell. The expression level of the gene product may be measured directly, for example, by assaying for the level of that gene product expressed in the plant or plant part thereof, or indirectly, for example, by measuring the activity of the gene product in the plant or plant part thereof using assays specific for the gene product of interest. The decreased expression may occur during and/or subsequent to growth of the plant to the desired stage of development. In specific examples, the expression polynucleotides and/or the polypeptides are modulated in monocots, including for example maize, rice, oat, sorghum, wheat, and barley.

A subject plant or plant cell is one in which genetic alteration, such as transformation, has been effected—as to a polynucleotide of interest, or is a plant or plant cell which is descended from a plant or cell so altered and which comprises the alteration. A control or control plant or control plant cell provides a reference point for measuring changes in phenotype of the subject plant or plant cell. A control plant or plant cell may comprise, for example: (a) a wild-type plant or cell of the same genotype as the starting material for the genetic alteration which resulted in the subject plant or cell; (b) a plant or plant cell of the same genotype as the starting material but which has been transformed with a null construct with a construct which has no known effect on the trait or phenotype of interest, such as a construct comprising only a marker gene; (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the recombinase or the inverted repeat is not expressed.

The expression of the hairpin RNA polynucleotide from the inverted repeat can be used for example to impart traits in plants. The inverted repeat can be designed to target any polynucleotide of interest or combination of polynucleotides wherein a decrease of expression of the polynucleotide provides for a desirable change in the plant, plant part, or seed of interest. In this manner, the inverted repeat is designed such that the encoded hairpin RNA targets one or more polynucleotides of interest including any cellular RNA such as, but not limited to, an endogenous RNA, a non-endogenous RNA, a viral RNA, an RNA transcribed from introduced vectors such as plasmids, an RNA transcribed from a transgene, and the like.

Target polynucleotides include, for example, those genes involved in information, such as zinc fingers, those involved in communication, such as kinases, and those involved in housekeeping, such as heat shock proteins. More specific categories of sequences for suppression, include, for example, sequences encoding traits that modulate insect/pathogen resistance, disease resistance, herbicide resistance, sterility, grain characteristics, oil production (including an increase in oleic acid levels, a modulation in saturated and/or unsaturated oils), starch, carbohydrate, phytate, fatty acid content, protein content, nutrient, plant vigor, nutrient content, phytic acid content, amino acid composition, tocol content, metabolism, digestability, kernel size, sucrose loading, increasing levels of lysine and sulfur, essential amino acids.

Additional target polynucleotides of interest include polynucleotides involved in primary and secondary biosynthetic pathways. Thus, for example, the polynucleotide targeted for suppression can be involved in amino acid and protein biosynthesis; nucleic acid biosynthesis; mineral nutrient uptake and transport; nitrogen and sulfur metabolism; photosynthesis and carbohydrate metabolism; cell wall biosynthesis; fatty acid metabolism; membrane biosynthesis; membrane transport processes; hormone biosynthesis; cytoskeleton biosynthesis; and the like. Other genes of interest include, but are not limited to, those involved in biotic and abiotic stress responses; those involved in signal perception; those involved in developmental processes such as vegetative and reproductive growth, dormancy, and senescence and programmed death; those involved in secondary metabolism; for example, biosynthesis of alkaloids, terpenoids, and phenylpropanoids; and the like. In other examples, the target gene of interest is one that upon suppression of the sequence there is in improved grain quality, enhanced yield, an improved feed value including more balanced amino acids and/or higher available energy, and improved wet milling characteristics including higher oil and/or reduced fiber.

The expression level of a polypeptide and/or an RNA may be measured directly, for example, by assaying for the level of the polypeptide or the RNA in the plant, or indirectly, for example, by measuring the activity of the polypeptide or the RNA in the plant. Inhibiting the expression of any given gene product of interest may occur during and/or subsequent to growth of the plant to the desired stage of development.

In some examples an AGP-like polypeptide is targeted for suppression. AGP catalyzes the first committed reaction in the pathway of starch synthesis. Numerous genes encoding the small and large subunits of AGP from plants have been described. See, for example, Smith-White et al. (1992) *J. Mol. Evol.* 34: 449-464, herein incorporated herein by reference in its entirety. The corresponding genes identified from maize are the endosperm specific Bt2 (GenBank Acc. No. AF334959) and Sh2 (GenBank Acc. No. AF334959) genes. See, for example, Bae et al. (1990) *Maydica* 35: 317-322; Bhave et al. (1990) *Plant Cell* 2 581-588; Deyner et al. (1996) *Plant Physiology* 112, 2 779-785; each of which is incorporated herein in its entirety by reference. Additional AGP polynucleotides include AGP1 and AGP2. AGP1 represents the large subunit of the embryo isoform, whereas AGP2 corresponds to the small subunit. See, for example, Giroux et al. (1995) *Plant Physiol.* 108: 1333-1334, U.S. Pat. No. 6,232,529, Hannah et. al. (2001) *Plant Physiol* 127: 173-183, U.S. patent application Ser. No. 11/021,666, published as US 2005-0160494, and Harvengt et al. (1996) *Plant Physiol.* 112: 1399 (Accession No. X96771), each of which is herein incorporated by reference.

Reducing or eliminating the level of at least one AGP polypeptide in the cell, plastids, and/or the cytoplasm will disrupt starch biosynthesis and/or enhance oil production. See, Stark et al. (1992) *Science* 258:287-292 and U.S. Pat. No. 6,262,529. Disrupting starch biosynthesis is any modification to the starch anabolic pathway that results in a net decrease in starch production when compared to a control plant. Disrupting storage of starch is any modification to the starch catabolic pathway that results in an increase in starch degradation and net decrease in starch accumulation. A decrease in the activity of an AGP-like polypeptide, such as AGP1 and AGP2, can be measured by assaying for the activity of ADP-glucose pyrophosphoylase directly (EC 2.7.7.27). Briefly, the activity is measured as described in Singletary et al. (1980) *Plant Physiol.* 92: 160-167, herein incorporated in its entirety by reference. Alternatively, the level of the polypeptide or the transcript can be assayed by Western analysis or Northern analysis, respectively. In some examples, the level is determined by assaying for the desired suppression phenotype.

In another example, at least one FAD is targeted for suppression. FADs of interest include, stearoyl-acyl-carrier-protein desaturase (Fad1; see U.S. Pat. No. 6,117,677), delta-15 desaturase (omega-3) (Fad3; Shah et al. (1997) *Plant Physiol.* 11:1533-1539), delta-4 (trans) desaturase (Fad4; Xiao et al. (2001) *J. Biol. Chem.* 276:31561-31566), delta-7 desaturase, (Fad5; see U.S. Pat. No. 6,635,451), omega-6 fatty-acid desaturase (Fad6; see U.S. Pat. No. 6,635,451), omega-3 fatty-acid desaturase (Fad7; Iba et al. (1993) *J. Biol. Chem.* 268:24099-24105), delta-5 desaturase (see U.S. Pat. No. 6,589,767), delta-9-desaturase (see U.S. Pat. No. 5,723,595), fatty acyl-CoA:fatty alcohol acyltransferase (wax synthase; see U.S. Pat. No. 6,492,509), beta-ketoacyl-ACP synthase in an antisense or sense orientation (see U.S. Pat. No. 6,483,008), and delta-12 fatty acid desaturase (FAD2), an enzyme that converts oleic acid to linoleic acid by introducing a double bond at the delta-12 position (Okuley et al. (1994) *Plant Cell* 6:147-58). Additional FAD2-like sequences include those disclosed in GenBank Accession No. NM_112047; GenBank Accession No. AF243045; European Patent No. EP0668919 B1; U.S. Pat. No. 6,291,742; U.S. Pat. No. 6,310,194; U.S. Pat. No. 6,323,392; U.S. Pat. No. 6,372,965; U.S. Patent Application Publication No. 20030033633; and U.S. Patent Application Publication No. 20030140372; all of which are incorporated in their entirety herein by reference. In maize, two FAD2 proteins have been identified: zmFAD2-1 and zmFAD2-2 (U.S. application Ser. No. 11/021,666, Kinney et al. (2001) *Biochem. Soc. Trans.* 30:1099-1103; and Mikkilineni et al. (2003) *Theor. Appl. Genet.* 106:1326-1332), each of which is herein incorporated by reference.

Reducing or eliminating the level of at least one FAD polypeptide in the cell, plastids, and/or the cytoplasm will modify the oil characteristics of the plant. FAD2, or a biologically active variant or fragment thereof, converts the delta-12 single bond of oleic acid (C18:1) into a conjugated double bond, thus producing linoleic acid (C18:2). Therefore, inhibiting the expression or function of FAD2 or a biologically active variant thereof prevents the conversion of oleic acid into linoleic acid, and thus, oleic acid accumulates in the plant or plant part thereof and the level of linoleic acid is decreased. Methods to assay for oleic acid and linoleic acid levels are known. See, for example, U.S. application Ser. No. 11/021,666, published as US 2005-0160494. Using the methods and compositions disclosed herein, total oil production can be increased and/or the characteristics of the oil can be modified. A modulation of oleic acid levels comprises any increase or decrease in oleic acid content when compared to a control plant or plant part. In one example, the oleic acid level is decreased or increased by 1%, 5%, 10%, 20%, 30%, 40%, 50%, 60%, 70%, 80%, 90%, or greater.

In other examples, sequences involved in phytic acid biosynthesis can be targeted for suppression. Phytic acid refers to myo-inositol tetraphosphoric acid, myo-inositol pentaphosphoric acid, or myo-inositol hexaphosphoric acid. As a salt with cations, phytic acid is called phytate. Phytic acid biosynthesis sequences which can be targeted for suppression include, but are not limited to, LPA1 (U.S. application Ser. No. 11/133,075,issued as U.S. Pat. No. 7,511,198). LPA2 (U.S. Publication No. 20050202486 and U.S. Publication No. 20030079247); LPA3 (U.S. application Ser. No. 11/132,864, published as US 2005-0289670; myo-inositol 1-phosphate synthase (MI1PS), inositol 1,3,4-trisphosphate 5/6 kinases (ITPKs) and myo-inositol monophophatase (IMP) (see WO 99/05298) and the like, the disclosures of which are herein incorporated by reference. See also, U.S. Pat. No. 6,855,869, herein incorporated by reference. Methods to assay for the level of phytic acid in a plant are known. See, for example, U.S. Pat. No. 6,111,168 and U.S. Application Publication 20030009011, both of which are herein incorporated by reference. As used herein, a modulation of phytic acid content comprises any increase or decrease in phytic acid level when compared to a control plant or plant part. In one example, the phytic acid level is decreased by 1%, 5%, 10%, 20%, 30%, 40%, 50%, 60%, 70%, 80%, 90%, or greater.

In other examples, a prolamin polypeptide can be targeted for suppression. Prolamins are the major endosperm storage protein of all cereal grains. The complete amino acid sequence of many prolamin polypeptides are know and has allowed the structure and properties of the prolamin superfamily to be characterized. See, Shewry et al. (1990) *Biochem Journal* 267:1-12 and Shewry et al. (2002) *Journal of Experimental Botany* 53:947-958. The prolamin polypeptides of maize (called zeins) are classified into the following classes: α-zeins, β-zeins, γ-zeins, and δ-zeins. See, Coleman et al. (1999) *Seed Proteins* Dordrecht: Kluwer Academic Publishers 109-139 and Leite et al. (1999) *Seed Proteins* Dordrecht: Kluwer Academic Publishers 141-157.

Any α-zein sequence can be targeted for suppression including, for example, a sequence encoding the 19K α-zein polypeptide or a biologically active variant or fragment thereof and a sequence encoding the 22K α-zein polypeptide or a biologically active variant or fragment thereof. See, for example, Segral et al. (2003) *Genetics* 165:387-397, GenBank Accession No. X61085, AF371277 and X55661, and Kim et al. (2004) *Plant Physiol.* 134 (1), 380-387; herein incorporated by reference. Any γ-zein sequence can be targeted, for example, sequences encoding the 50 kD γ-zein polypeptide (GenBank Acc. No. AF371263 and U.S. Pat. No. 6,858,778), the 16 kD γ-zein polypeptide (GenBank Acc. No. AF371261), or a biologically active variant or fragment thereof. Any δ-zein sequence can be targeted including, for example, a polynucleotide encoding the 10 kD δ-zein polypeptide (GenBank Accession No. AF371266) and the 18 kD δ-zein polypeptide (GenBank Acc. No. AF371265), or a biologically active variant or fragment thereof.

In other examples, a lysine-ketoglutarate reductase (LKR) (EC 1.5.1.8) is targeted for suppression. LKR is the first enzyme in the lysine catabolism pathway (also named as Lys 2-oxoglutarate reductase) which condenses Lys and alpha-ketoglutarate into saccharopine and uses the co-factor NADPH. The nucleotide and amino acid sequence of many LKR polypeptides are known. See, for example, Miron et al. (2000) *Plant Physiology* 123:655-663, Kemper et al. (1999) *The Plant Cell* 11:1981-1993, and, Epelbaum et al. (1997) *Plant Molecular Biology* 35:735-748, each of which is herein incorporated by reference.

Decreasing or eliminating the level of at least one prolamin polypeptide and/or an LKR polypeptide can, for example, improve the amino acid composition/nutrient value of the seed, improve digestibility and nutrient availability, improve response to feed processing, improve silage quality, and/or increase efficiency of the wet or dry milling process. See, for example, U.S. Pat. No. 6,858,778, herein incorporated by reference, for assays to measure these various qualities. Alternatively, the level of the polypeptide or the transcript can be assayed by Western analysis or Northern analysis, respectively. In specific examples, a γ-zein gene is suppressed to increase the nutritional value of seed, particularly by increasing the lysine content of the seed, and/or the digestibility of seed. Increases in the lysine content of such seed can be at least about 10%, 15%, 20%, 25%, 30%, 35%, 40%, 45%, and 50% or higher. Digestibility can be improved by at least 3%, 6%, 9%, 12%, 15%, 20% and greater. See, for example, U.S. Pat. No. 6,858,778, herein incorporated by reference, for assays to measure these various qualities.

In other, the targeted gene for suppression may be in a different organism. The production of a inverted repeat may be made in a plant or plant part, and RNA RNA target a gene within the pathogen to decrease the viability of the pathogen, and/or the impact of the pathogen on the host. For example a Fire et al. (U.S. Pat. No. 6,506,559) and Plaetineck et al., (WO 00/01846) each of which is herein incorporated by reference.

The following examples are offered by way of illustration and not by way of limitation.

EXPERIMENTAL

Example 1

Vectors Containing the Inverted Repeat (IR) Precursor Cassette

The vectors outlined below in Table 4 are generated using standard molecular biology methods. Table 4 schematically outlines four gene configurations that contain an inverted repeat precursor cassette. Following integration of one of the four constructs into the plant genome, FLP recombinase activity is supplied. In examples 1-3, the oppositely oriented FRT sites invert the intervening sequence, producing the two functional expression cassettes highlighted in grey. In example 4, the FRT1 sites recombine to delete the intervening sequence and produce the functional expression cassette.

TABLE 4

GZ - GZ3 which is the Gamma Zein terminator sequence, which is included as a spacer to reduce the likelihood of any read through into the PDS-OP sequence.
Note: OP = inverted orientation of the sequence
STOP = STOP codon to prevent translation Functional transcriptional cassettes formed after recombination shown in grey

| 1 | | | | | | | | | | | | |
|---|---|---|---|---|---|---|---|---|---|---|---|---|
| Before Recombination | UBI PRO | UBI INTRON | FRT1 | PDS-OP | UBI INTRON-OP | UBI PRO-OP | Spacer | PinII-OP | YFP-OP | FRT1-OP | PDS-OP | |
| After FLP-mediated Inversion | UBI PRO | UBI INTRON | FRT1 | YFP | PinII | | Spacer | UBI PRO | UBI INTRON | PDS | FRT1-OP | PDS-OP |

| 2 | | | | | | | | | | |
|---|---|---|---|---|---|---|---|---|---|---|
| Before Recombination | UBI PRO | UBI INTRON | PDS | FRT1 | UBI INTRON-OP | UBI PRO-OP | Spacer | PDS | FRT1-OP | YFP | PinII |
| After FLP-mediated Inversion | UBI PRO | UBI INTRON | PDS | FRT1 | PDS-OP | | Spacer | UBI PRO | UBI INTRON | FRT1-OP | YFP | PinII |

| 3 | | | | | | | | | | | | |
|---|---|---|---|---|---|---|---|---|---|---|---|---|
| Before Recombination | UBI PRO | UBI INTRON | PDS | STOP | FRT1 | YFP | PinII | Spacer | PDS | FRT1-OP | UBI INTRON-OP | UBI PRO-OP |
| After FLP-mediated Inversion | UBI PRO | UBI INTRON | PDS | STOP | FRT1 | PDS-OP | Spacer | PinII-OP | YFP-OP | FRT1-OP | UBI INTRON-OP | UBI PRO-OP |

| 4 | | | | | | | | | |
|---|---|---|---|---|---|---|---|---|---|
| Before Recombination | UBI PRO | UBI INTRON | PDS | FRT1 | UBI PRO/INTRON | YFP | PinII | GZ 3' | FRT1 | PDS-OP |
| After FLP-mediated Inversion | UBI PRO | UBI INTRON | PDS | FRT1 | PDS-OP | | | | | |

Example 2

DNA Delivery Methods

Transformation of the inverted repeat precursor cassette along with the expression cassette UBI::moPAT-CFPm::pinII into genotype Hi-II follows a well-established bombardment transformation protocol used for introducing DNA into the scutellum of immature maize embryos (Songstad et al. (1996) *In Vitro Cell Dev. Biol. Plant* 32: 179-183). It is noted that any suitable method of transformation can be used, such as *Agrobacterium*-mediated transformation and many other methods. Cells are transformed by culturing maize immature embryos (approximately 1-1.5 mm in length) onto medium containing N6 salts, Erikkson's vitamins, 0.69 g/l proline, 2 mg/l 2,4-D and 3% sucrose. After 4-5 days of incubation in the dark at 28° C., embryos are removed from the first medium and cultured onto similar medium containing 12% sucrose. Embryos are allowed to acclimate to this medium for 3 h prior to transformation. The scutellar surface of the immature embryos is targeted using particle bombardment. Embryos are transformed using the PDS-1000 Helium Gun from Bio-Rad at one shot per sample using 650PS1 rupture disks. DNA delivered per shot averages 0.1667 µg. Following bombardment, all embryos are maintained on standard maize culture medium (N6 salts, Erikkson's vitamins, 0.69 g/l proline, 2 mg/l 2,4-D, 3% sucrose) for 2-3 days and then transferred to N6-based medium containing 3 mg/L Bialaphos®. Plates are maintained at 28° C. in the dark and are observed for colony recovery with transfers to fresh medium every two to three weeks. Recovered colonies and plants are scored based on CFP visual expression, leaf painting sensitivity to a 1% application of Ignite® herbicide, and molecular characterization via PCR and Southern analysis.

Transformation of the inverted repeat precursor cassette and the expression cassette UBI::moPAT-CFPm::pinII into Hi-II immature embryos is done using the *Agrobacterium* mediated DNA delivery method, as described by U.S. Pat. No. 5,981,840 with the following modifications. It is noted that any suitable method of transformation can be used, such as particle-mediated transformation, as well as many other methods. *Agrobacteria* are grown to the log phase in liquid minimal A medium containing 100 µM spectinomycin. Embryos are immersed in a log phase suspension of *Agrobacteria* adjusted to obtain an effective concentration of $5 \times 10^8$ cfu/ml. Embryos are infected for 5 minutes and then co-cultured on culture medium containing acetosyringone for 7 days at 20° C. in the dark. After 7 days, the embryos are transferred to standard culture medium (MS salts with N6 macronutrients, 1 mg/L 2,4-D, 1 mg/L Dicamba, 20 g/L sucrose, 0.6 g/L glucose, 1 mg/L silver nitrate, and 100 mg/L carbenicillin) with 3 mg/L Bialaphos® as the selective agent. Plates are maintained at 28° C. in the dark and are observed for colony recovery with transfers to fresh medium every two to three weeks. Recovered colonies and plants are scored based on CFP visual expression, leaf painting sensitivity to a 1% application of Ignite® herbicide, and molecular characterization via PCR and Southern analysis.

Example 3

Using Recombinase Mediated Inversions to Generate Inverted Repeat Expression Units In Planta Inversion inverted repeat precursor cassettes designed to invert the sequence flanked by the two FRT sites are shown in numbers 1-3 in Table 4. Such cassettes contain identical recombinase target sites (FRT1) flanking the sequence to be inverted, and the two FRT1 sites are in opposite orientation relative to each other.

Stable transgenic callus events are generated using *Agrobacterium*-mediated transformation. Within the T-DNA borders are both the "inverted repeat precursor" cassette (i.e. one of the examples in #1-3, in Table 4) and the selection cassette 35S::bar::pinII. Bialaphos selection is used to recover transgenic callus events, and QPCR is used to identify single copy integrations. Such single-copy transgenic calli are used for a second round of DNA delivery. In this second-round transformation, a plasmid containing Ubi::FLP::pinII is introduced into the callus cells using particle gun delivery. In this configuration, recombination results in inversion. In vectors 1-3 above, inversion of the intervening sequence results in two functional changes to the cassette; activation of transcription for both the visual marker (Yellow Fluorescence Protein) and the newly created inverted repeat. In 1-3 above, activated transcription of the Phytoene Desaturase inverted repeat (PDS/PDS-OP) results in silencing of the endogenous Phytoene Desaturase, blocking carotenoid biosynthesis resulting in photobleaching of leaves when the plants are placed in the light. The activated marker, in this case YFP, is used to follow cell lines that contain the inverted sequence and the newly-formed "Gene-of-interest Inverted Repeat".

Example 4

Using Recombinase Mediated Deletion to Generate Functional Inverted-Repeat Expression Unit In Planta An excision inverted repeat precursor cassette that will undergo FLP-mediated excision is shown in # 4 in Table 4. This cassette contains identical recombinase target sites (FRT1) flanking the sequence to be excised, and the two FRT1 sites are in the same orientation relative to each other.

Stable transgenic callus events are generated using *Agrobacterium*-mediated transformation. Within the T-DNA borders are both the "inverted repeat precursor" cassette (i.e. #4 in Table 4) and the selection cassette UBI PRO-Ubi intron-moPAT~CFP-pinII. Bialaphos selection is used to recover transgenic callus events, and QPCR is used to identify single copy integrations. Such single-copy transgenic calli are used for a second round of DNA delivery. In this second-round transformation, a plasmid containing Ubi::FLP::pinII is introduced into the callus cells using particle gun delivery. With the FRT1 sites being in the same orientation in the inverted repeat precursor locus, recombination results in deletion of the intervening sequence, bringing the two components of the Inverted Repeat sequence into functional proximity, and allowing transcription of the phytoene desaturase IR sequence (designated PDS/PDS-OP in #4, Table 4). Transcription of this IR sequence results in silencing of the endogenous Phytoene Desaturase, blocking carotenoid biosynthesis resulting in photobleaching of leaves when the plants are placed in the light. The marker gene in the inverted repeat precursor cassette, in this case YFP, is deleted during the recombination process, permitting the loss-of-phenotype to act as a screen for cell lineages that contain the newly generated PDS-IR. Activity of the moPAT~CFP expression cassette remains unaltered and can still be use to follow the transgenic locus.

Example 5

Using Inducible Recombinase Mediated Inversions to Generate Inverted-Repeat Expression Unit In Planta Inversion inverted repeat precursor cassettes designed to invert the sequence flanked by the two FRT sites are shown in numbers 1-3 in Table 4. Such cassettes contain identical recombinase target sites (FRT1) flanking the sequence to be inverted, and the two FRT1 sites are in opposite orientation relative to each other.

Stable transgenic callus events are generated using *Agrobacterium*-mediated transformation. Within the T-DNA borders are the "inverted repeat precursor" cassette (i.e. #1-3 in Table 4), a selection cassette 35S::bar::pinII, the tetracycline-inducible FLP components, Ubi::TetR::pinII and 35S-Tet-Operator::FLP::pinII. Bialaphos selection is used to recover transgenic callus events, and QPCR is used to identify single copy integrations. Once stable transgenic lines have been produced, 0.5 mg/l tetracycline or 0.2 mg/l deoxycycline can be added to the culture media or applied to plant parts. These ligands induce FLP expression and with the FRT1 sites in the IR-precursor cassette in the opposite orientation, recombination results in inversion. In vectors 1-3 above, inversion of the intervening sequence results in two functional changes to the cassette; activation of transcription for both the visual marker (Yellow Fluorescence Protein) and the newly created inverted repeat. In 1-3 above, activated transcription of the Phytoene Desaturase inverted repeat (PDS/PDS-OP) results in silencing of the endogenous Phytoene Desaturase, blocking carotenoid biosynthesis resulting in photobleaching of leaves when the plants are placed in the light. The activated marker, in this case YFP, is used to follow cell lines that contain the inverted sequence and the newly-formed "Gene-of-interest Inverted Repeat".

Example 6

Crossing Recombinase Containing Plants with the Inverted Repeat Precursor Cassette Containing Plant to Generate Inverted Repeat Expression Units In Planta Inversion inverted repeat precursor cassettes designed to invert the sequence flanked by the two FRT sites are shown in numbers 1-3 in Table 4. Such cassettes contain identical recombinase target sites (FRT1) flanking the sequence to be inverted, and the two FRT1 sites are in opposite orientation relative to each other.

Stable transgenic callus events are generated using *Agrobacterium*-mediated transformation. Within the T-DNA borders are the "inverted repeat precursor" cassette (i.e. #1-3 in Table 4) and UBI:ubi intron::GAT::pinII. After *Agrobacterium*-mediated transformation, glyphosate selection is used to recover transgenic callus events, and QPCR is used to identify single copy integrations. Such single-copy transgenic calli are regenerated and the resultant plants grown in the greenhouse. Plants are also grown in the greenhouse that contain the cassette for tetracycline-inducible FLP expression. When the inverted repeat precursor containing plants and the tetracycline-inducible FLP plants reach maturity, reciprocal crosses are preformed between individuals in these two classes. Upon crossing, either 0.5 mg/l tetracycline or 0.2 mg/l deoxycycline can be applied to the progeny at various timepoints.

To produce progeny plants in which the inverted-repeat expression cassette is found uniformly throughout the plant, tetracycline can be applied to the parent ear shortly after pollination. In this scenario, 10 ml of a 0.2 mg/l deoxycycline solution is injected beneath the husk leaves. The solution is transported throughout the immature ear, and deoxycycline-induced FLP expression results in inversion of the inverted repeat precursor cassette in the zygote (producing a plant that is non-chimeric for the inverted sequence). In vectors 1-3 above, inversion of the intervening sequence results in two functional changes to the cassette; activation of transcription for both the visual marker (Yellow Fluorescence Protein) and the newly created inverted repeat. In 1-3 above, activated transcription of the Phytoene Desaturase inverted repeat (PDS/PDS-OP) results in silencing of the endogenous Phytoene Desaturase, blocking carotenoid biosynthesis and resulting in photobleaching of leaves when the plants are placed in the light. The activated marker, in this case YFP, is used to follow cell lines that contain the inverted sequence and the newly-formed "Gene-of-interest Inverted Repeat".

To produce chimeric plants, 0.2 mg/l deoxycycline is added after the zygote stage. For example, coleoptilar-stage embryos 0.5-0.7 mm in length) can be removed from the developing kernel and placed on embryo rescue medium containing, 0.2 mg/l deoxycycline. After two days under dark culture conditions, the embryos are transferred to fresh medium with no ligand, upon which they continue to develop, mature and eventually germinate. The resultant plants are transferred to the greenhouse and screened for activation of both the marker gene and the Gene-of-interest IR. Both phenotypic and molecular analyses confirm that large sectors of the plant contain the inverted functional sequence.

Adding ligand during later stages of embryo development, during plant growth, or during development of reproductive structures (tassel and ear) is also effective at generating the FLP-mediated inversion and producing the resultant new phenotypes.

Example 7

Delivery of Both the Inverted Repeat Precursor Cassette and the Recombinase to Produce Functional Inverted-Repeat Expression Units In Vivo A modified version of inverted repeat precursor cassette #1 (Table 4) is produced, that upon inversion will produce both a functional UBI:ubi intron::moPAT~YFP::pinII and a functional UBI:ubiintron::PDS~FRT1~PDS-OP. This IR-precursor plasmid and a plasmid containing a UBI:ubi intron::FLP::pinII expression cassette are co-delivered in scutellar cells of immature embryos using well established particle gun methods. After co-delivery, expression of FLP results in inversion of the FRT-flanked sequence, activating both PAT~YFP and PDS/PDS-OP expression. Bialaphos selection (and yellow fluorescence) is used to recover the stable transgenic events carrying the in vivo-produced IR expression cassette. PCR primers for the FLP gene are used to verify that the FLP expression cassette did not integrate.

Other methods of DNA delivery can also in a similar manner, including electroporation, microinjection, PEG- or liposome-mediated delivery, as well as *Agrobacterium*.

Example 8

Crossing FLP Recombinase Containing Plants with an Insertion Inverted Repeat Precursor Cassette Containing Plant to Generate Inverted Repeat Expression Units In Planta An insertion inverted repeat precursor cassette and a transfer cassette are designed as indicated below:
Insertion inverted repeat precursor cassette:
UBI Pro::UBI intron::PDS-OP::FRT1::YFP::PinII::FRT5::CFP::pinII
Transfer cassette: FRT1::spacer::PDS::UBI PRO-Ubi intron: FRT5.
The target site (shaded grey) and the transfer cassette contain the FRT1 and FRT5 recombination sites. These sites are dissimilar and non-recombinogenic with respect to one another.

Stable transgenic callus events having either the transfer cassette or the insertion inverted repeat precursor cassette are generated using *Agrobacterium*-mediated transformation. Two T-DNA constructs are produced and two separate *Agrobacterium* transformations are preformed. For the first construct, within the T-DNA borders are the transfer cassette and UBI PRO-Ubi intron::GAT::pinII. For the second construct, within the T-DNA borders are the "inverted repeat precursor" cassette+UBI PRO-Ubi intron::GAT;;pinII+UBI PRO-Ubi intron::TetR::pinII+35S:Tet Operator:FLP::pinII. After *Agrobacterium*-mediated transformation, glyphosate selection is used to recover transgenic callus events, and QPCR is used to identify single copy integrations. Such single-copy transgenic calli for both the transfer cassette line and the insertion inverted repeat precursor cassette line are regenerated and the resultant plants grown in the greenhouse. When the inverted repeat precursor containing plants and the transfer cassette containing plants reach maturity, they are crossed. Upon crossing, either 0.5 mg/l tetracycline or 0.2 mg/l deoxycycline can be applied to the progeny at various time points.

To produce progeny plants in which the functional inverted repeat expression unit is found uniformly throughout the plant, tetracycline can be applied to the parent ear shortly after pollination. In this scenario, 10 ml of a 0.2 mg/l deoxycycline solution is injected beneath the husk leaves. The solution is transported throughout the immature ear, and deoxycycline-induced FLP expression results in the integration of the transfer cassette into the target site of the insertion inverted repeat precursor cassette in the zygote (producing a plant that is non-chimeric for the functional inverted repeat expression unit). Insertion of the transfer cassette results in two functional changes to the cassette; the loss of transcription for the visual marker (Yellow Fluorescence Protein) and activation of transcription the inhibitory hairpin RNA polynucleotide. Activated transcription of the Phytoene Desaturase inverted repeat (PDS/PDS-OP) results in silencing of the endogenous Phytoene Desaturase, blocking carotenoid biosynthesis and resulting in photobleaching of leaves when the plants are placed in the light.

Example 9

Providing Recombinase and Two Transfer Cassette to a Plant with an Insertion Inverted Repeat Precursor Cassette to Generate Inverted Repeat Expression Units In Planta Recombinase target sites can be used to directionally integrate complementary linear DNA fragments into an "SSI inverted repeat precursor site". Before introducing sequences of interest for silencing, an acceptor site must be generated. Within the T-DNA borders is UBI PRO-Ubi intron:FRT1:RFP-pinII:FRT87+UBI PRO-Ubi intron-GAT-pinII. After *Agrobacterium*-mediated transformation, transformed events are selected on glyphosate-containing medium, and molecular analysis is used to screen events for single copy number. All single copy events are regenerated, and plants are grown in the greenhouse. This population of transgenic plants are analyzed for high levels of both RFP and GAT expression using either QrtPCR or Westerns. Single copy events that support strong transgene expression are grown to maturity. Progeny immature embryos are then used for the next phase of screening; testing these transgenic loci for recombination. A new donor construct is used for these tests, consisting of FRT1:YFP-pinII:FRT12:SPACER Seq:FRT6:Spacer Seq:FRT87. This donor cassette does not contain a promoter, so YFP is not expressed until Site-Specific Intregration (SSI) occurs. This is accomplished by introducing the donor cassette+UBIPRO-Ubi intron:FLP-pinII into the scutellar cells using the particle gun, Successful cassette replacement at the acceptor locus results in loss of RFP and GAT expression and gain of YFP expression. Proper site specific recombination is further confirmed through PCR across the newly created FRT1 and FRT87 hybrid junctions. Acceptor sites that have been confirmed to support strong transgene expression and be good sites for recombination are now ready for introduction of complementary sequences for in vivo formation of an inverted repeat expression cassette iva SSI. Note that the reconfigured acceptor site now contains a strong constitutive promoter with four downstream dissimilar FRT sites, known not to cross react with each other. To generate the inverted repeat expression cassette in the plant cell, two complementary sequences are introduced to the cell along with FLP activity. The first such fragment is FRT1:PDS-OP:FRT12 and the second fragment is FRT6:PDS:FRT87. These DNA fragments are co-injected into zygote cells along with a plasmid containing UBI PRO-Ubi intron-FLP-pinII. The FLP expression cassette is transiently expressed and is later confirmed through molecular analysis not to have randomly integrated. This transient FLP activity, however, is enough to catalyze site specific integration of the two FRT-flanked fragments, generating the functional inverted repeat expression cassette UBI PRO-Ubi intron: FRT1:PDS-OP:FRT12:SPACER: FRT6:PDS:FRT87. Activated transcription of the Phytoene Desaturase inverted repeat (PDS/PDS-OP) results in silencing of the endogenous Phytoene Desaturase, blocking carotenoid biosynthesis and resulting in photobleaching of leaves when the plants are placed in the light.

Example 10

Maize Transformation via Particle Bombardment

Immature maize embryos from greenhouse donor plants are bombarded with a plasmid containing the polynucleotide of interest and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.
Preparation of Target Tissue The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the polynucleotide of the system described herein operably linked to a promoter is made. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the appropriate phenotypic trait associated with gene in transformation construct.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 11

Agrobacterium-Mediated Transformation of Maize

For *Agrobacterium*-mediated transformation of maize with a sequence of interest of the invention, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the nucleotide sequence(s) of interest to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 12

Microinjection-Mediated Transformation of the Maize Zygote

Microinjection of Maize Zygotes in Isolated Embryo Sacs is performed according to the methods described in Laurie et al. (1999) *In Vitro Cellular and Developmental Biology— Plant* 35:320-325, and in U.S. Pat. No. 6,300,543, both herein incorporated by reference.

Embryo sacs containing zygotes are isolated in 250-300 micron-thick sections produced using a vibratome. DNA (100 µg) is vacuum-dried in Tris-EDTA buffer and dissolved in 0.5 ml milli-Q water. The resulting preparation is divided into 10 ml aliquots and stored at −20° C. until use. Microinjection pipettes are pulled from borosilicate tubing (1.0 mm×0.75 mm, Sutter Instrument Co.) on a micropipette puller (P-97, Sutter Instrument Co.), bevelled to a tip diameter of 1 to 5 mm with a pipette grinder (BV-10, Sutter Instrument Co.) and autoclaved. After being loaded with plasmid using a microloader (Eppendorf), the microinjection pipette is connected to a Transjector 5246 (Eppendorf). The injection unit of the Transjector is mounted on a three-dimensional manipulator attached to a Stereomicroscope. The angle between the injection pipette and the section is about 45°. The microscope that supports the micromanipulator and injection unit is housed in a laminar flow hood. The tip of the injection micropipette is brought to the surface of sections by means of a micromanipulator. The tip of the injection micropipette is brought just above the target cells, either the zygote or the central cell. Penetration of a cell is achieved using an hydraulic joystick. Injection volume are adjusted with injection pressure and injection time to about 1 pl. Approximately 100 to 120 embryo sacs are injected per hour. Within one week of culture approximately 71% of the isolated embryo sacs produce endosperm. The remaining embryo sacs, which fail to develop endosperm, only rarely produce an embryo. Embryos develop in approximately 60% of the embryo sacs that produce endosperm.

Recovery and Characterization of Transgenic Plants Produced from Transformed Zygotes Following microinjection of zygotes, embryo sacs are cultured at 25° C. for 5 days in the dark on modified MS medium containing 0.4 mg/L L-asparagine, 0.1 mg/L 6-benzylaminopurine (BAP) and 15% sucrose at pH 5.8. as described in Campenot et al. (1992) *Amer. J. Bot* 79:1368. Endosperm enlargement is observed after 5 days in culture. Embryo sacs are then transferred to modified MS medium containing 0.4 mg/L L-asparagine and 10% sucrose at pH 5.8 and no BAP. Following incubation for another 5 days in the dark, embryos are transferred to modified MS medium containing 0.4 mg/L L-asparagine and 3% sucrose at pH 5.8 and no BAP. When young shoots are approximately 1.5 cm long they are exposed to light. Seedlings are then transferred to a nutrient solution at pH 6.5 as per Zhang et al. (1990) *Plant Physiol.* 94:577.

Example 13

Delivery of a attP Containing Transfer Cassette into a Plant Containing an Insertion Inverted Repeat Precursor Cassette to Generate Inverted Repeat Expression Units In Planta An insertion inverted repeat precursor cassette and a transfer cassette are designed as indicated below:
Insersion inverted repeat precursor cassette:
UBI Pro:: UBI intron::PDS-OP::attB::bar::pinII
Transfer cassette: attP::Spacer::PDS::UBI PRO-Ubi intron
The target site (shaded grey) and the transfer cassette contain an attB or an attP recombination site, respectively. These sites are dissimilar, recombinogenic sites whose recombination is catalyzed by phiC31.

Stable transgenic callus events having the insertion inverted repeat precursor cassette are generated using *Agrobacterium*-mediated transformation. Within the T-DNA borders are the "inverted repeat precursor" cassette+UBI PRO-Ubi intron::GAT;;pinII. After *Agrobacterium*-mediated transformation, glyphosate selection is used to recover transgenic callus events, and QPCR is used to identify single copy integrations. Such single-copy transgenic calli are regenerated and the resultant plants grown in the greenhouse. When the inverted repeat precursor containing plants reach maturity, they are crossed, and immature embryos are harvested when the embryos are between 0.9 and 1.5 mm in length. The immature embryos are placed axis-side down, and a particle gun is used to delivery the transfer cassette (as a circular plasmid) along with a second plasmid containing the expression cassette UBI PRO-Ubi intron::ΦC31::pinII into the scutellar cells. The ΦC31 recombinase expressed after co-delivery of these plasmids catalyzes recombination between the attP sequence in the inverted repeat precursor locus and the attB site located in the transfer cassette plasmid, inserting the plasmid sequence at this site and forming the following new recombined locus: UBI Pro:: UBI intron::PDS-OP::attL::Spacer::PDS::UBI PRO-Ubi intron:attR:bar::pinII. Formation of this recombined locus produces a functional inverted repeat expression cassette and activates bar expression which can be used to select for cells and growing callus that contain the inverted repeat expression cassette. Activated transcription of the Phytoene Desaturase inverted repeat (PDS/PDS-OP) results in silencing of the endogenous Phytoene Desaturase, blocking carotenoid biosynthesis and resulting in photobleaching of leaves when the plants are placed in the light.

Example 14

Soybean Embryo Transformation Prophetic Example

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 μE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein et al. (1987) *Nature*, 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the DNA of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing DNA of interest are cut from the agarose gel. DNA is purified from the agarose using the GELase digesting enzyme following the manufacturer's protocol.

A 50 μl aliquot of sterile distilled water containing 3 mg of gold particles (3 mg gold) is added to 5 μl of a 1 μg/μl DNA solution (either intact plasmid or DNA fragment prepared as described above), 50 μl 2.5M CaCl$_2$ and 20 μl of 0.1 M spermidine. The mixture is shaken 3 min on level 3 of a vortex shaker and spun for 10 sec in a bench microfuge. After a wash with 400 μl 100% ethanol the pellet is suspended by sonication in 40 μl of 100% ethanol. Five μl of DNA suspension is dispensed to each flying disk of the Biolistic PDS1000/HE instrument disk. Each 5 μl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB 196 media and cultured as described above. Six to seven days post-bombardment, the SB196 is exchanged with fresh SB 196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB 196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB 166, for 1-2 weeks. Clusters are then subcultured to medium SB103 for 3 weeks. During this period, individual embryos can be removed from the clusters and screened for the desired phenotpye. It should be noted that any detectable phenotype, resulting from the expression of the genes of interest, could be screened at this stage.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm |
| pH 5.8 | |

| FN Lite Stock Solutions | | | |
|---|---|---|---|
| Stock # | | 1000 ml | 500 ml |
| 1 | MS Fe EDTA 100x Stock | | |
| | Na$_2$ EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL—Cat# 11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat# 11117-066); 1 ml B5 vitamins 1000× stock; 60 g maltose; 750 mg MgCl$_2$ hexahydrate; 5 g activated charcoal; pH 5.7; and, 2 g gelrite.

SB 103 solid medium (per liter) comprises: 1 pkg. MS salts (Gibco/BRL—Cat# 11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat# 21153-036); pH 5.7; and, 5 g TC agar. 2,4-D stock is obtained premade from Phytotech cat# D 295—concentration is 1 mg/ml.

B5 Vitamins Stock (per 100 ml) which is stored in aliquots at −20C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide

The invention claimed is:

1. A method for producing an inverted repeat in a plant or plant part comprising
   a) introducing into the genome of the plant or the plant part a polynucleotide comprising an inverted repeat precursor cassette, wherein said inverted repeat precursor cassette comprises a first DNA segment and a target site, wherein said target site is flanked by a first and a second functional recombination site, wherein said first and second recombination sites are dissimilar and non-recombinogenic with respect to one another;

b) introducing into the plant or plant part a second polynucleotide comprising a second DNA segment having sufficient sequence complementarity to the first DNA segment to form, upon transcription of a functional inverted repeat expression unit, an inhibitory hairpin RNA polynucleotide, and said second DNA segment is flanked by said first and said second recombination sites, such that recombination inserts said second DNA segment into said target site in the opposite orientation to said first DNA segment; and, c) introducing into said plant or plant part a recombinase, wherein said recombinase mediates a recombination event in said inverted repeat precursor cassette and thereby produces the functional inverted repeat expression unit.

2. The method of claim 1, wherein said inverted repeat is expressed in said plant or said plant part.

3. The method of claim 1, wherein the first DNA segment comprises at least about 20 nucleotides having at least 90% sequence complementary to a target polynucleotide of interest; and, the second DNA segment comprises at least about 20 nucleotides having at least 85% sequence complementarity to the first DNA segment.

4. The method of claim 3, wherein the first polynucleotide comprises the following in 5' to 3' or the 3' to 5' orientation: the first DNA segment, a third DNA segment and said target site flanked by the first and the second recombination sites, wherein the third DNA segment is of sufficient length to allow the inverted repeat to be transcribed as a hairpin RNA.

5. The method of claim 3, wherein said second polynucleotide comprises the following in 5' to 3' or the 3' to 5' orientation: the first recombination site, a third DNA segment, the second DNA segment, and said second recombination site wherein the third DNA segment is of sufficient length to allow the inverted repeat to be transcribed as a hairpin RNA.

6. The method of claim 1, wherein the recombinase comprises a FLP recombinase, a Cre recombinase, a lambda integrase, a SSVI integrase, or a φ31C integrase.

7. The method of claim 1, wherein the recombinase is encoded by a polynucleotide stably integrated into a genome of the plant or the plant part.

8. The method of claim 1, wherein the recombinase is encoded by a polynucleotide operably linked to a constitutive, inducible, developmentally regulated, or tissue-preferred promoter active in the plant or the plant part.

9. The method of claim 1, wherein said recombinase is transiently provided in the plant or plant part.

10. The method of claim 1, wherein the inverted repeat is operably linked to a constitutive, inducible, developmentally regulated, or tissue-preferred promoter.

11. The method of claim 1, wherein said plant or plant part is a monocot or a dicot.

12. The method of claim 11, wherein said plant or plant part is selected from the group consisting of maize, barley, millet, wheat, sorghum, oat, rice, soybean, canola, alfalfa, sunflower, safflower, tobacco, *Arabidopsis*, and cotton.

13. The method of claim 1, wherein said plant part comprises a plant cell.

* * * * *